US008653235B2

(12) United States Patent
Hirai et al.

(10) Patent No.: US 8,653,235 B2
(45) Date of Patent: Feb. 18, 2014

(54) CYCLIC PEPTIDE COMPOUND OR PHARMACOLOGICALLY ACCEPTABLE SALT THEREOF AND METHOD FOR PRODUCING SAME

(75) Inventors: Yohei Hirai, Hyogo (JP); Yoji Okugawa, Hyogo (JP)

(73) Assignee: Kwansei Gakuin Educational Foundation, Hyogo (JP)

( * ) Notice: Subject to any disclaimer, the term of this patent is extended or adjusted under 35 U.S.C. 154(b) by 0 days.

(21) Appl. No.: 13/808,772
(22) PCT Filed: Jul. 6, 2011
(86) PCT No.: PCT/JP2011/065521
§ 371 (c)(1), (2), (4) Date: Jan. 7, 2013
(87) PCT Pub. No.: WO2012/005313
PCT Pub. Date: Jan. 12, 2012

(65) Prior Publication Data
US 2013/0109833 A1 May 2, 2013

(30) Foreign Application Priority Data
Jul. 8, 2010 (JP) .................... 2010-155576

(51) Int. Cl.
A61K 38/00 (2006.01)
C07K 2/00 (2006.01)
C07K 4/00 (2006.01)
C07K 5/00 (2006.01)
C07K 7/00 (2006.01)

(52) U.S. Cl.
USPC ............................ 530/300; 530/317; 514/1.1

(58) Field of Classification Search
None
See application file for complete search history.

(56) References Cited

U.S. PATENT DOCUMENTS 5,998,579 A 12/1999 Koshida

FOREIGN PATENT DOCUMENTS

| JP | 10007698 A | 1/1998 |
| JP | 2003146998 A | 5/2003 |
| JP | 3922345 B2 | 3/2007 |

OTHER PUBLICATIONS

Bascom et al., "Epimorphin Overexpression in the Mouse Mammary Gland Promotes Alveolar Hyperplasia and Mammary Adenocarcinoma," Cancer Res, 2005, 65(19):8617-8621.
Choi et al., "The changes of stratum corneum interstices and calcium distribution of follicular epithelium of experimentally induced comedoens (EIC) by oleic acid," Exp Dermatol, 1997, 6:29-35.
Hirai et al., "Epimorphin: A Mesenchymal Protein essential for Epithelial Morphogenesis," Cell, 1992, 69:471-481.
Hirai et al., "Epimorphin Functions as a Key Morphoregulator for Mammary Epithelial Cells," J Cell Biol, 1998, 140 (1):159-169.
Hirai et al., "Structural optimization of pep7, a small peptide extracted from epimorphin, for effective induction of hair follicle anagen," Experimental Dermatology, 2005, 14:692-699.

Koshida and Hirai, "Identification of Cellular Recognition Sequence of Epimorphin and Critical Role of Cell/Epimorphin Interaction in Lung Branching Morphogenesis," Biochemical and Biophysical Research Communications, 1997, 234:522-525.
Maeda, "An Electron Microscopic Study of Experimentally-induced Comedo Effects of Vitamin A Acid on Comedo Formation," Journal of Dermatology, 1991, 18:397-407.
Oka et al., "Epimorphin acts extracellularly to promote cell sorting and aggregation during the condesation of vertebral cartilage," Developmental Biology, 2006, 291:25-37.
Okugawa et al., "Epimorphin-derived peptide antagonists remedy epidermal parakeratosis triggered by unsaturated fatty acid," Journal of Dermatological Science, 2010, 59:176-183.
Radisky et al., "Single proteins might have dual but related functions in intracellular and extracellular microenvironments," Natrue Reviews Molecular Cell Biology, 2009, 10:228-234.
Shaker et al., "Epimorphin deletion protects mice from inflammation-induced colon carcinogenesis and alters stem cell niche myofibroblast secretion," J Clin Invest, 2010, 120:2081-2093.
Takebe et al., "Epimorphin acts to induce hair follicle anagen in C57BL/6 mice," FASEB Journal, 2003, 17 (14):2037-2047.
Yamada et al., "Involvement of epimorphin in the repair of experimental renal fibrosis in mice," Laboratory Investigation, 2010, 90:867-880.
International Search Report, mailed Sep. 13, 2011, for International Patent Application PCT/JP2011/065521, 2 pages.
English Abstract for JP10-007698, 2 pages.
English Abstract for JP2003-146988 and JP3922345, 1 page.

*Primary Examiner* — Cecilia J Tsang
*Assistant Examiner* — Sergio Coffa
(74) *Attorney, Agent, or Firm* — Casimir Jones, S.C.

(57) ABSTRACT

Provided are a cyclic peptide compound or a pharmacologically acceptable salt thereof capable of inhibiting parakeratosis of skin, and a method for producing the same. This method comprises subjecting a cyclic peptide compound of Formula (I):

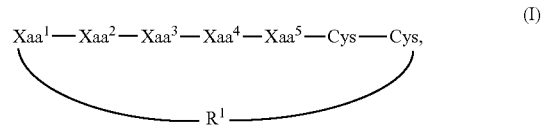

or a pharmacologically acceptable salt thereof, wherein $Xaa^1$ and $Xaa^5$ are each optionally substituted Ser, optionally substituted Thr, or optionally substituted Tyr; $Xaa^2$ is optionally substituted Ile, optionally substituted Val, or optionally substituted Leu; $Xaa^3$ and $Xaa^4$ are each optionally substituted Asn, optionally substituted Gln, optionally substituted Asp, or optionally substituted Glu; and $R^1$ is a group of Formula (II):

$$—CO—(CH_2)_n—NH— \quad (II),$$

or Formula (III):

$$—NH—(CH_2)_n—CO— \quad (III),$$

wherein n is the same as defined above, and in Formula (I), the linkage between Cys and Cys is a peptide bond or a disulfide bond, and the other linkages are peptide bonds,
to cyclization with a compound of Formula (IV):

$$Cys\text{-}R^1\text{-}Xaa^1\text{-}Xaa^2\text{-}Xaa^3\text{-}Xaa^4\text{-}Xaa^5\text{-}Cys \quad (IV),$$

wherein, $Xaa^1$, $Xaa^2$, $Xaa^3$, $Xaa^4$, $Xaa^5$, and $R^1$ are the same as defined above.

10 Claims, 9 Drawing Sheets

- Endogenous epimorphin
- β actin

HaCaT-TE cells  - Secreted epimorphin

PT67-TE cells  - Secreted epimorphin

```
                      SEQUENCE LISTING

<160> NUMBER OF SEQ ID NOS: 8

<210> SEQ ID NO 1
<211> LENGTH: 7
<212> TYPE: PRT
<213> ORGANISM: Artificial
<220> FEATURE:
<223> OTHER INFORMATION: A sequence of a cyclic peptide compound.
<220> FEATURE:
<221> NAME/KEY: MISC_FEATURE
<222> LOCATION: (1)..(1)
<223> OTHER INFORMATION: Xaa is Ser which may have a substituent, Thr
      which may have a substituent or Tyr which may have a substituent.
<220> FEATURE:
<221> NAME/KEY: NON_TER
<222> LOCATION: (1)..(1)
<223> OTHER INFORMATION: Xaa is bound to seventh amino acid (Cys)
      through R1 (R1 means g-CO-(CH2)n-NH- hor g-NH-(CH2)n-CO-h,
      wherein n is an integer of 1 to 10.).
<220> FEATURE:
<221> NAME/KEY: MISC_FEATURE
<222> LOCATION: (2)..(2)
<223> OTHER INFORMATION: Xaa is Ile which may have a substituent, Val
      which may have a substituent or Leu which may have a substituent.
<220> FEATURE:
<221> NAME/KEY: MISC_FEATURE
<222> LOCATION: (3)..(3)
<223> OTHER INFORMATION: Xaa is Asn which may have a substituent, Gln
      which may have a substituent, Asp which may have a substituent or
      Glu which may have a substituent.
<220> FEATURE:
<221> NAME/KEY: MISC_FEATURE
<222> LOCATION: (4)..(4)
<223> OTHER INFORMATION: Xaa is Asn which may have a substituent, Gln
      which may have a substituent, Asp which may have a substituent or
      Glu which may have a substituent.
<220> FEATURE:
<221> NAME/KEY: MISC_FEATURE
<222> LOCATION: (5)..(5)
<223> OTHER INFORMATION: Xaa is Ser which may have a substituent, Thr
      which may have a substituent or Tyr which may have a substituent.
```

```
<220> FEATURE:
<221> NAME/KEY: DISULFID
<222> LOCATION: (6)..(7)
<223> OTHER INFORMATION: Cys is bound to Cys by disulfide binding or
      peptide binding.
<220> FEATURE:
<221> NAME/KEY: NON_TER
<222> LOCATION: (7)..(7)
<223> OTHER INFORMATION: Cys is bound to the first amino acid (Xaa)
      through R1 (R1 means g-CO-(CH2)n-NH-hor g-NH-(CH2)n-CO-h, wherein
      n is an integer of 1 to 10.).

<400> SEQUENCE: 1

Xaa Xaa Xaa Xaa Xaa Cys Cys
1               5

<210> SEQ ID NO 2
<211> LENGTH: 6
<212> TYPE: PRT
<213> ORGANISM: Artificial
<220> FEATURE:
<223> OTHER INFORMATION: A partial sequence of a linear peptide or a
      cyclic peptide compound.

<400> SEQUENCE: 2

Ser Ile Glu Gln Ser Cys
1               5

<210> SEQ ID NO 3
<211> LENGTH: 7
<212> TYPE: PRT
<213> ORGANISM: Artificial
<220> FEATURE:
<223> OTHER INFORMATION: A sequence of a linear peptide.

<400> SEQUENCE: 3

Ser Ile Glu Gln Ser Cys Asp
1               5

<210> SEQ ID NO 4
<211> LENGTH: 7
<212> TYPE: PRT
<213> ORGANISM: Artificial
<220> FEATURE:
<223> OTHER INFORMATION: A linear amino acid sequence before cyclization
      for a cyclic peptide compound
<220> FEATURE:
<221> NAME/KEY: NON_CONS
<222> LOCATION: (1)..(2)
<223> OTHER INFORMATION: Cys is bound to Xaa through R1 (R1 means g-CO-
      (CH2)n-NH- hor g-NH-(CH2)n-CO-h, wherein n is an integer of 1 to
      10.).
<220> FEATURE:
<221> NAME/KEY: MISC_FEATURE
<222> LOCATION: (2)..(2)
<223> OTHER INFORMATION: Xaa is Ser which may have a substituent, Thr
      which may have a substituent or Tyr which may have a substituent.
<220> FEATURE:
<221> NAME/KEY: MISC_FEATURE
<222> LOCATION: (3)..(3)
<223> OTHER INFORMATION: Xaa is Ile which may have a substituent, Val
      which may have a substituent or Leu which may have a substituent.
<220> FEATURE:
<221> NAME/KEY: MISC_FEATURE
<222> LOCATION: (4)..(4)
<223> OTHER INFORMATION: Xaa is Asn which may have a substituent, Gln
      which may have a substituent, Asp which may have a substituent or
      Glu which may have a substituent.
<220> FEATURE:
<221> NAME/KEY: MISC_FEATURE
<222> LOCATION: (5)..(5)
<223> OTHER INFORMATION: Xaa is Asn which may have a substituent, Gln
      which may have a substituent, Asp which may have a substituent or
      Glu which may have a substituent.
```

```
<220> FEATURE:
<221> NAME/KEY: MISC_FEATURE
<222> LOCATION: (6)..(6)
<223> OTHER INFORMATION: Xaa is Ser which may have a substituent, Thr
      which may have a substituent or Tyr which may have a substituent.

<400> SEQUENCE: 4

Cys Xaa Xaa Xaa Xaa Xaa Cys
1               5

<210> SEQ ID NO 5
<211> LENGTH: 867
<212> TYPE: DNA
<213> ORGANISM: Mus sp.

<400> SEQUENCE: 5
atgaaggacc gaacccagga gctccgcacg gccaaggaca gcgatgacga cgacgatgtc      60
actgtcactg tggaccgaga ccgcttcatg gatgaattct ttgaacaggt ggaagagatc     120
cggggcttta ttgacaagat tgccgaaaac gtggaggagt gaagcggaa acacagcgcc      180 atcctggcct ccccgaaccc cgatgagaag acaaaggagg aactggagga gctcatgtcg     240
gacattaaga agacagcgaa caaagttcgc tccaagctaa agagcattga gcagagcatc     300
gagcaggagg aaggtctgaa ccgctcatca gccgacctga ggatccggaa gacgcagcac     360
tccacgctgt cccgaaagtt tgtggaggtc atgtccgagt acaacgccac tcagtcagac     420
taccgagaac gctgcaaagg gcgcatccag aggcagctgg agatcaccgg ccggaccacg     480
accagtgagg aattggaaga catgctggag agtgggaacc ctgccatctt tgcctctggg     540
atcatcatgg actccagcat ctcgaagcag gccctcagtg agatcgagac cagacacagt     600
gagatcatca gctggagac cagcatccgg gagctgcacg acatgttcat ggacatggcc     660
atgctggtgg agagccaggg ggagatgatt gacaggatcg agtacaatgt ggagcacgcc     720
gtggactacg tggagagggc cgtgtcagac accaagaagg ccgtcaagta ccagagcaag     780
gcgcgcagga agaagatcat gatcatcatt tgctgtgtga ttctgggcat catcatcgcc     840
tccaccatcg ggggcatctt tggatag                                         867

<210> SEQ ID NO 6
<211> LENGTH: 39
<212> TYPE: DNA
<213> ORGANISM: Artificial
<220> FEATURE:
<223> OTHER INFORMATION: T7-tagged sequence.

<400> SEQUENCE: 6
atggctagca tgactggtgg acagcaaatg ggtcggatc                             39

<210> SEQ ID NO 7
<211> LENGTH: 63
<212> TYPE: DNA
<213> ORGANISM: Artificial
<220> FEATURE:
<223> OTHER INFORMATION: A sequence of IL-2 signal peptide

<400> SEQUENCE: 7
atgtacagca tgcagctcgc atcctgtgtc acattgacac ttgtgctcct tgtcaacagc      60
gct                                                                   63

<210> SEQ ID NO 8
<211> LENGTH: 8
<212> TYPE: PRT
<213> ORGANISM: Artificial
```

-continued

```
<220> FEATURE:
<223> OTHER INFORMATION: A linear amino acid sequence before cyclization
      for a cyclic peptide compound

<400> SEQUENCE: 8

Cys Gly Ser Ile Glu Gln Ser Cys
1               5
```

CYCLIC PEPTIDE COMPOUND OR PHARMACOLOGICALLY ACCEPTABLE SALT THEREOF AND METHOD FOR PRODUCING SAME

TECHNICAL FIELD

The present invention relates to a cyclic peptide compound or a pharmacologically acceptable salt thereof, and a method for producing the same. More specifically, the present invention relates to a cyclic peptide compound or a pharmacologically acceptable salt thereof useful in preventing, treating, or ameliorating abnormal skin conditions caused by parakeratosis, and a method for producing the same.

BACKGROUND ART

Human epidermis is composed of, from deep to superficial, stratum basale, stratum spinosum, stratum granulosum, and stratum corneum. In normal human skin, the stratum corneum has a barrier function to protect skin from physical and chemical stimulation.

In normal skin, cell turnover generally occurs in a 28-day cycle. In normal skin cell turnover, keratinocytes are pushed upward from the stratum granulosum to the stratum corneum. At this time, keratinocytes are differentiated and enucleated to cause a loss of nucleated cells, forming a mature stratum corneum. However, when, for example, cell turnover occurs in an overly rapid manner, enucleation does not occur in the final stage of keratinocyte differentiation, and the stratum corneum is thereby put in the condition of parakeratosis, causing a significant decrease in the skin barrier function. Application of oleic acid to skin also causes the same condition as parakeratosis (Non-Patent Document 1).

Epimorphin is considered to be one of the factors involved in regulation of epithelial morphogenesis (Non-Patent Documents 2 to 5). There has also been a report that in epimorphin knockout mice, the induction of malignant transformation is decreased (see, for example, Non-Patent Document 6).

In order to regulate epithelial morphogenesis, oligopeptides, which inhibit the epithelial morphogenesis-promoting activity of epimorphin, have been suggested (see, for example, Patent Documents 1 and 2).

However, the inhibitory action of oligopeptides on the epithelial morphogenesis-promoting activity is not sufficient to regulate epithelial morphogenesis. Therefore, there has been a demand for a more useful compound that can inhibit with high efficiency, for example, the occurrence of abnormal morphology and abnormal differentiation of epithelial cells of skin, etc., induced by epimorphin.

CITATION LIST

Patent Documents

Patent Document 1: JP10-007698A
Patent Document 2: JP3922345B

Non-Patent Documents

Non-Patent Document 1: Experimental Dermatology, 1997, volume 6, pp. 29-35
Non-Patent Document 2: The Journal of Dermatology, 1991, volume 18, pp. 397-401
Non-Patent Document 3: Cell, 1992, volume 69, pp. 471-481
Non-Patent Document 4: Journal of Cell Biology, 1998, volume 140, pp. 159-169
Non-Patent Document 5: Nature Reviews Molecular Cell Biology, 2009, volume 10, pp. 228-234
Non-Patent Document 6: Epimorphin deletion protects mice from inflammation-induced colon carcinogenesis and alters stem cell niche myofibroblast secretion, Anisa Shaker et al., The Journal of Clinical Investigation, May 10, 2010, volume 120, pp. 2081-2093
Non-Patent Document 7: Laboratory Investigation, 2010, volume 90, pp. 867-880
Non-Patent Document 8: Cancer Research, 2005, volume 65, pp. 8617-8621
Non-Patent Document 9: Developmental Biology, 2006, volume 291, pp. 25-37

SUMMARY OF INVENTION

Technical Problem

The present invention has been made in view of the above-described problems of the prior art. An object of the present invention is to provide a cyclic peptide compound or a pharmacologically acceptable salt thereof capable of inhibiting the occurrence of abnormal conditions of human skin induced by epimorphin or oleic acid. The present invention also aims to provide a method for producing the cyclic peptide compound or a pharmacologically acceptable salt thereof. This method can easily produce the cyclic peptide compound or a pharmacologically acceptable salt thereof.

Solution to Problem

Specifically, the present invention is summarized as below.
(1) A cyclic peptide compound represented by Formula (I):

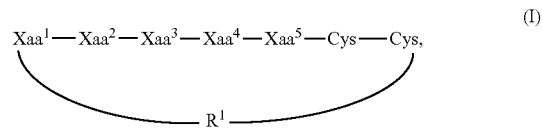

or a pharmacologically acceptable salt thereof, wherein
$Xaa^1$ and $Xaa^5$ are each independently optionally substituted seryl, optionally substituted threonyl, or optionally substituted tyrosinyl;
$Xaa^2$ is optionally substituted isoleucyl, optionally substituted valyl, or optionally substituted leucyl;
$Xaa^3$ and $Xaa^4$ are each independently optionally substituted asparaginyl, optionally substituted glutaminyl, optionally substituted aspartyl, or optionally substituted glutamyl;
Cys is cysteinyl; and
$R^1$ is a group represented by either Formula (II):

$$-CO-(CH_2)_n-NH- \quad (II),$$

wherein n is an integer of 1 to 10, or Formula (III):

$$-NH-(CH_2)_n-CO- \quad (III),$$

wherein n is an integer of 1 to 10; and in Formula (I), the linkage between Cys and Cys is a peptide bond or a disulfide bond, and the other linkages are peptide bonds.
(2) The cyclic peptide compound or a pharmacologically acceptable salt thereof according to Item (1), wherein in Formula (I), $Xaa^1$ is seryl, $Xaa^2$ is isoleucyl, $Xaa^3$ is glutamyl, $Xaa^4$ is glutaminyl, $Xaa^5$ is seryl, and $R^1$ is a group represented by Formula (III) wherein n is 1.

(3) A method for producing a cyclic peptide compound represented by Formula (I):

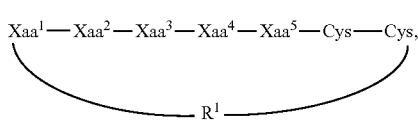

or a pharmacologically acceptable salt thereof,
wherein $Xaa^1$ and $Xaa^5$ are each independently optionally substituted seryl, optionally substituted threonyl, or optionally substituted tyrosinyl;
$Xaa^2$ is optionally substituted isoleucyl, optionally substituted valyl, or optionally substituted leucyl;
$Xaa^3$ and $Xaa^4$ are each independently optionally substituted asparaginyl, optionally substituted glutaminyl, optionally substituted aspartyl, or optionally substituted glutamyl;
Cys is cysteinyl; and
$R^1$ is a group represented by either Formula (II):

wherein n is an integer of 1 to 10, or Formula (III):

wherein n is an integer of 1 to 10; and in Formula (I), the linkage between Cys and Cys is a peptide bond or a disulfide bond, and the other linkages are peptide bonds,
the method comprising cyclizing a compound represented by Formula (IV):

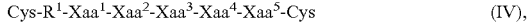

wherein $Xaa^1$, $Xaa^2$, $Xaa^3$, $Xaa^4$, $Xaa^5$, Cys, and $R^1$ are the same as $Xaa^1$, $Xaa^2$, $Xaa^3$, $Xaa^4$, $Xaa^5$, Cys, and $R^1$ of Formula (I).

Advantageous Effects of Invention

The cyclic peptide compound or a pharmacologically acceptable salt thereof of the present invention acts antagonistically on epimorphin and regulates the biological activity thereof. Therefore, the cyclic peptide compound or a pharmacologically acceptable salt thereof of the present invention achieves an excellent effect, i.e., the occurrence of abnormal conditions of human skin induced by epimorphin or oleic acid can be inhibited. On the basis of such an effect, the cyclic peptide compound or a pharmacologically acceptable salt thereof of the present invention is useful as an active ingredient of pharmaceutical preparations. Further, the cyclic peptide compound or a pharmacologically acceptable salt thereof of the present invention can be used as a reagent for controlling, in particular, for inhibiting the activity of epimorphin in an experimental system for clarifying or verifying the functions and properties of epimorphin. The cyclic peptide compound or a pharmacologically acceptable salt thereof of the present invention is also useful as a reagent or a control for evaluating the activities and actions of epimorphin or an epimorphin agonist, as it being an epimorphin antagonist.) Additionally, according to the method for producing a cyclic peptide compound or pharmacologically acceptable salt thereof of the present invention, an excellent effect can be achieved, i.e., the cyclic peptide compound or pharmacologically acceptable salt can be easily produced.

BRIEF DESCRIPTION OF DRAWINGS

FIG. 1 is a photograph serving as a drawing and showing the relationship between oleic acid and the level of expression of endogenous epimorphin in HaCaT cells investigated in Reference Example 1.

FIG. 2 is a photograph serving as a drawing and showing the relationship between oleic acid and the level of expression of endogenous epimorphin in each of the HaCaT-TE cell culture supernatant and PT67-TE cell culture supernatant investigated in Reference Example 2.

FIG. 3 is a chart showing the mass spectrum of the peptide obtained in Example 1.

FIG. 4 is a chart showing the mass spectrum of the oxidized peptide obtained in Example 1.

FIG. 5 (B) is a photograph serving as a drawing and showing the morphology of the cell cluster in which the medium of Experimental No. 10 is used in Test Example 2.

FIG. 6 is a graph showing the results obtained by examining the relationship between the kind of medium and the lumen formation rate in Test Example 2.

FIG. 7 (B) is a photograph serving as a drawing and showing the morphology of the cell cluster in which the medium of Experimental No. 14 is used in Test Example 3.

FIG. 8 is a graph showing the results obtained by examining the relationship between the kind of medium and the lumen formation rate in Test Example 3.

FIG. 9 is a graph showing the results obtained by examining the relationship between the kind of medium and the cornified envelope formation rate in Test Example 4.

FIG. 10 is a graph showing the results obtained by examining the relationship between the kind of medium or cell and the cornified envelope formation rate in Test Example 5.

FIG. 11 is a graph showing the results obtained by examining the relationship between the kind of sample and the epidermal thickness in Test Example 6.

FIG. 12 is a graph showing the results obtained by examining the relationship between the kind of sample and the ratio of the dyed cells to the total cells in Test Example 6.

FIG. 13 (B) is a photograph serving as a drawing and showing the results obtained by observing the tissue morphology of the cell construct to which a 0.5 volume % oleic acid-containing ethanol solution and the sample of Experimental No. 37 are applied in Test Example 7. FIG. 13 (C) is a photograph serving as a drawing and showing the results obtained by observing the tissue morphology of the cell construct to which a 0.5 volume % oleic acid-containing ethanol solution and the sample of Experimental No. 38 are applied in Test Example 7. FIG. 13 (D) is a photograph serving as a drawing and showing the results obtained by observing the tissue morphology of the cell construct to which a 0.5 volume % oleic acid-containing ethanol solution and the sample of Experimental No. 39 are applied in Test Example 7.

DESCRIPTION OF EMBODIMENTS

Figure 1:
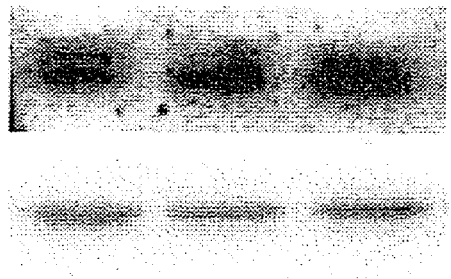
[FIG. 1]

1. Cyclic Peptide Compound or Pharmacologically Acceptable Salt

The cyclic peptide compound or a pharmacologically acceptable salt thereof of the present invention has a structure (SEQ ID NO: 1) represented by Formula (I):

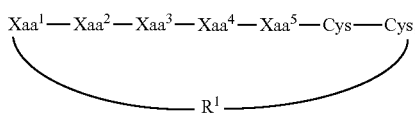 (I)

wherein $Xaa^1$ and $Xaa^5$ are each independently optionally substituted seryl, optionally substituted threonyl, or optionally substituted tyrosinyl;
$Xaa^2$ is optionally substituted isoleucyl, optionally substituted valyl, or optionally substituted leucyl;
$Xaa^3$ and $Xaa^4$ are each independently optionally substituted asparaginyl, optionally substituted glutaminyl, optionally substituted aspartyl, or optionally substituted glutamyl;
Cys is cysteinyl; and
$R^1$ is a group represented by either Formula (II):

$$—CO—(CH_2)_n—NH—$$ (II), wherein n is an integer of 1 to 10, or Formula (III):

$$—NH—(CH_2)_n—CO—$$ (III), wherein n is an integer of 1 to 10; and in Formula (I), the linkage between Cys and Cys is a peptide bond or a disulfide bond, and the other linkages are peptide bonds.

The present inventors found the following.
(A) In both cases where a human skin model is brought into contact with oleic acid and where exogenous epimorphin is expressed in a human skin model, a similar abnormality in tissue morphology occurs in the skin model.
(B) Although a straight-chain peptide (Ser-Ile-Glu-Gln-Ser-Cys-Asp, SEQ ID NO: 3) comprising the amino acid sequence of Ser-Ile-Glu-Gln-Ser-Cys (SEQ ID NO: 2) does not inhibit the occurrence of abnormality in tissue morphology of the skin model induced by epimorphin or oleic acid, a cyclic peptide compound and a pharmacologically acceptable salt thereof inhibit the occurrence of abnormality in tissue morphology, the cyclic peptide compound comprising the amino acid sequence of SEQ ID NO: 2, the peptide with this amino acid sequence being cyclized with a cysteinyl group added to this peptide chain by linking it to the cysteinyl group of this peptide chain through a disulfide or peptide bond, and with a group represented by Formula (II).
The present invention has been made based on these findings.

The cyclic peptide compound or a pharmacologically acceptable salt thereof of the present invention has a significant feature in that it has a structure represented by Formula (I). As such, the cyclic peptide compound or a pharmacologically acceptable salt thereof of the present invention has, in the molecule, a structure in which the peptide chain having the amino acid sequence of SEQ ID NO: 2 is cyclized with an cysteinyl group added to this peptide chain by linking it to the cysteinyl group of this peptide chain through a disulfide or peptide bond, and with a group represented by Formula (II) or (III). Therefore, the cyclic peptide compound or a pharmacologically acceptable salt thereof of the present invention can inhibit the occurrence of abnormal conditions of human tissue, etc., induced by epimorphin or oleic acid. Hereinafter, the action of inhibiting the occurrence of abnormal conditions induced in human tissue, etc., by epimorphin or oleic acid is sometimes simply referred to as "inhibitory action."

$Xaa^1$ is optionally substituted seryl, optionally substituted threonyl, or optionally substituted tyrosinyl. The substituent may be any functional group, as long as it does not impair the effects of the present invention. Examples of the substituents include thioglycosyl derived from monosaccharide or polysaccharide, O-glycosyl derived from monosaccharide or polysaccharide, N-glycosyl derived from monosaccharide or polysaccharide, phosphate, and the like. Among those mentioned as $Xaa^1$, seryl is preferable from the viewpoint of sufficiently exerting the inhibitory action.

$Xaa^2$ is optionally substituted isoleucyl, optionally substituted valyl, or optionally substituted leucyl. The substituent may be any functional group, as long as it does not impair the effects of the present invention. Examples of the substituents include alkyl having 1 to 3 carbon atoms, and the like. Specific examples thereof include methyl, ethyl, propyl, and the like. Among those mentioned as $Xaa^2$, isoleucyl is preferable from the viewpoint of sufficiently exerting the inhibitory action.

$Xaa^3$ is optionally substituted asparaginyl, optionally substituted glutaminyl, optionally substituted aspartyl, or optionally substituted glutamyl. The substituent may be any functional group, as long as it does not impair the object of the present invention. When $Xaa^3$ is optionally substituted asparaginyl, examples of the substituents include thioglycosyl derived from monosaccharide or polysaccharide, O-glycosyl derived from monosaccharide or polysaccharide, N-glycosyl derived from monosaccharide or polysaccharide, and the like. When $Xaa^3$ is optionally substituted glutaminyl, examples of the substituents include amino and the like. When $Xaa^3$ is optionally substituted aspartyl, examples of the substituents include succinimide, phosphate, and the like. When $Xaa^3$ is optionally substituted glutamyl, examples of the substituents include carboxyl and the like. Among those mentioned as $Xaa^3$, glutamyl is preferable from the viewpoint of sufficiently exerting the inhibitory action.

$Xaa^4$ is optionally substituted asparaginyl, optionally substituted glutaminyl, optionally substituted aspartyl, or optionally substituted glutamyl. The substituent may be any functional group, as long as it does not impair the effects of the present invention. Examples of the substituents include the same substituents as those mentioned above in relation to $Xaa^3$. Among those mentioned as $Xaa^4$, glutaminyl is preferable from the viewpoint of sufficiently exerting the inhibitory action.

$Xaa^5$ is optionally substituted seryl, optionally substituted threonyl, or optionally substituted tyrosinyl. The substituent may be any functional group, as long as it does not impair the effects of the present invention. Examples of the substituents include the same substituents as those mentioned above in relation to $Xaa^1$. Among those mentioned above as $Xaa^5$, seryl is preferable from the viewpoint of sufficiently exerting the inhibitory action.

In Formula (I), n is an integer of 1 to 10. From the viewpoint of sufficiently exerting the inhibitory action, n is 10 or less, preferably 8 or less, more preferably 5 or less, furthermore preferably 3 or less, and particularly preferably 1.

$Xaa^1$ to $Xaa^5$, $R^1$, and Cys may each be a L- or D-configuration. From the viewpoint of applicability to the human skin, each of $Xaa^1$ to $Xaa^5$, $R^1$, and Cys is preferably a L-configuration.

Examples of the pharmacologically acceptable salts include acid addition salts and base addition salts. Examples of acid addition salts include inorganic acid salts, organic acid salts, and the like. Examples of inorganic acid salts include hydrochloride, hydrobromate, sulfate, hydroiodide, nitrate, phosphate, and the like. Examples of organic acid salts include citrate, oxalate, acetate, formate, propionate, benzoate, trifluoroacetate, maleate, tartrate, methanesulfonate, benzenesulfonate, p-toluenesulfonate, and the like. Examples of base addition salts include inorganic base salts, organic base salts, and the like. Examples of inorganic base salts include sodium salt, potassium salt, calcium salt, magnesium salt, ammonium salt, and the like. Examples of organic base salts include triethyl ammonium salt, triethanol ammonium salt, pyridinium salt, diisopropylammonium salt, and the like.

Among the cyclic peptide compounds represented by Formula (I) and pharmacologically acceptable salts thereof, a compound represented by Formula (I), wherein $Xaa^1$ is seryl, $Xaa^2$ is isoleucyl, $Xaa^3$ is glutamyl, $Xaa^4$ is glutaminyl, $Xaa^5$ is seryl, and $R^1$ is a group represented by Formula (III) wherein n is 1 is preferable from the viewpoint of sufficiently exerting the inhibitory action.

The inhibitory action of the cyclic peptide compound or a pharmacologically acceptable salt thereof of the present invention can be evaluated based on improvement in abnormality of keratinocyte morphology achieved by, for example:
(a) applying the cyclic peptide compound of the present invention to the surface of differentiated cellular architecture obtained by three-dimensionally culturing keratinocytes expressing epimorphin on a support;
(b) applying oleic acid to the surface of differentiated cellular architecture obtained by three-dimensionally culturing keratinocytes on a support, followed by further application of the cyclic peptide compound of the present invention;
(c) embedding cell aggregates of keratinocytes expressing epimorphin in collagen gel, and culturing the cell aggregates in a medium containing the cyclic peptide compound of the present invention;
(d) embedding cell aggregates of keratinocytes in collagen gel, and culturing the cell aggregates in a medium containing oleic acid and the cyclic peptide compound of the present invention;
(e) culturing keratinocytes expressing epimorphin in a medium containing the cyclic peptide compound of the present invention, followed by culturing the obtained keratinocytes in a medium containing a calcium ionophore; or
(f) culturing keratinocytes in a medium containing the cyclic peptide compound of the present invention and oleic acid, followed by culturing the obtained keratinocytes in a medium containing a calcium ionophore.

The cyclic peptide compound or a pharmacologically acceptable salt thereof of the present invention acts antagonistically on epimorphin and inhibits the biological activity thereof, thereby enabling the occurrence of abnormal conditions of human tissue induced by epimorphin or oleic acid to be inhibited. The cyclic peptide compound or a pharmacologically acceptable salt thereof of the present invention is thus useful, for example, for inhibiting parakeratosis, etc., of human skin, promoting or inhibiting hair growth, and regenerating blood vessels, etc.; and is useful as an active ingredient of pharmaceutical preparations, quasi drugs, and cosmetics, and also as a reagent, etc., for evaluating the aforementioned actions. Therefore, the cyclic peptide compound or a pharmacologically acceptable salt thereof of the present invention can improve abnormal conditions in humans caused by parakeratosis by inhibiting parakeratosis of human skin. The cyclic peptide compound or a pharmacologically acceptable salt thereof of the present invention is therefore useful for use in improving abnormal conditions of human skin caused by parakeratosis. Examples of the abnormal conditions of human skin include skin roughness, pimples, calluses, warts, psoriasis, and the like.

Epimorphin is known to be involved in organ formation, etc., via the receptor tyrosine kinase that is present in endodermal cells. Overexpression of epimorphin may possibly result in diseases, such as chronic rheumatoid arthritis, cancers (e.g., renal cell carcinoma, skin cancer), arteriosclerosis, connective tissue disease, hematopoietic organ disease, renal disease, muscular dystrophy, osteoporosis, neurofibromatosis, Sturge-Weber syndrome, nodular sclerosis, neural tube closure defects, segmentation abnormalities, porencephaly, and hydrocephalus (Laboratory Investigation, 2010, volume 90, pp. 867-880 (Non-Patent Document 7); Cancer Research, 2005, volume 65, pp. 8617-8621 (Non-Patent Document 8); and Developmental Biology, 2006, volume 291, pp. 25-37 (Non-Patent Document 9)). The cyclic peptide compound or a pharmacologically acceptable salt thereof of the present invention can inhibit the biological activity of epimorphin, and is thus useful in treating damage in organs, such as lung, liver, kidney, stomach, and intestine; regenerating blood vessels; preventing and treating chronic arteriosclerosis obliterans, and Buerger's disease; and the like. It is also useful in preventing or treating diseases resulting from overexpression of epimorphin. Therefore, the cyclic peptide compound or a pharmacologically acceptable salt thereof of the present invention is useful as a pharmaceutical preparation, such as a prophylactic or therapeutic agent for diseases resulting from overexpression of epimorphin; a prophylactic or therapeutic agent for chronic arteriosclerosis obliterans, Buerger's disease, and the like; and a therapeutic agent for treating damaged organs.

In the aforementioned pharmaceutical preparation, the cyclic peptide compound or a pharmacologically acceptable salt thereof of the present invention may be supported on a pharmacologically acceptable carrier that is suitable for being introduced into an organ, a local site, tissue, or the like.

In the pharmaceutical preparation, the cyclic peptide compound or a pharmacologically acceptable salt thereof of the present invention is contained in a therapeutically effective amount. The amount varies depending on the application purpose, administration route, type of target diseases or damaged organs, dosage form, etc., of the pharmaceutical preparation. The amount can be suitably adjusted according to the application purpose, administration route, type of target diseases or damaged organs, dosage form, etc., of the pharmaceutical preparation. In general, the cyclic peptide compound or a pharmacologically acceptable salt thereof of the present invention is contained in the pharmaceutical preparation in an amount of 0.0001 to 100 mass %.

The pharmaceutical preparation may further contain other auxiliary agents according to the application purpose, administration route, type of target diseases or damaged organs, dosage form, etc., of the pharmaceutical preparation. Examples of the auxiliary agents include pharmacologically acceptable auxiliaries, excipients, binders, stabilizers, buffers, solubilizing agents, isotonic agents, and the like, which act to inhibit the decomposition of the cyclic peptide compound or a pharmacologically acceptable salt thereof of the present invention until the pharmaceutical preparation reaches the target site where the effect of the cyclic peptide compound or pharmacologically acceptable salt thereof of the present invention is to be expressed.

The dosage form of the pharmaceutical preparation varies since a suitable dosage form varies depending on, for example, the types of the target disease or damaged organs. It is preferable that the dosage form be suitably determined according to the types of the target disease or damaged organs. Examples of dosage forms of the aforementioned pharmaceutical preparation include a tablet, a capsule, a granule, a powder, a pill, a syrup, an injection, and the like.

The administration route of the pharmaceutical preparation varies depending on the application purpose, type of target diseases or damaged organs, age and body weight of a target human subject, etc., of the pharmaceutical preparation. It is preferable that the administration route be suitably determined according to the application purpose, type of target diseases or damaged organs, the age and body weight of a target human subject, etc., of the pharmaceutical preparation. Examples of the administration route of the pharmaceutical preparation include local administration, subcutaneous injection, intramuscular injection, intravenous injection, oral administration, and the like.

The dosage of the pharmaceutical preparation varies depending on the application purpose, type of target diseases or damaged organs, age and body weight of a target human subject, etc., of the pharmaceutical preparation. It is preferable that the dosage of the pharmaceutical preparation be suitably determined according to the application purpose, type of target diseases or damaged organs, age and body weight of a human subject, etc., of the pharmaceutical preparation. For example, when a target human subject is an adult, in order to sufficiently inhibit the biological activity of epimorphin, the amount of the cyclic peptide compound or a pharmacologically acceptable salt thereof of the present invention is preferably 1 μg or more, and more preferably 10 μg or more, per kg of the adult body weight per day; and in order to reduce the burden to the target human subject, the dosage of the pharmaceutical preparation is preferably adjusted to 10 mg or less, and more preferably 1 mg or less.

2. Method for Producing Cyclic Peptide Compound or Pharmacologically Acceptable Salt Thereof The method for producing a cyclic peptide compound or a pharmacologically acceptable salt thereof of the present invention is a method for producing a cyclic peptide compound represented by Formula (I) or a pharmacologically acceptable salt thereof. This method has a feature in that it comprises cyclizing a compound (SEQ ID NO: 4) represented by Formula (IV):

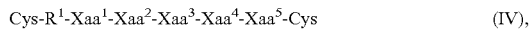

Cys-R$^1$-Xaa$^1$-Xaa$^2$-Xaa$^3$-Xaa$^4$-Xaa$^5$-Cys  (IV), wherein Xaa$^1$, Xaa$^2$, Xaa$^3$, Xaa$^4$, Xaa$^5$, Cys, and R$^1$ are the same as Xaa$^1$, Xaa$^2$, Xaa$^3$, Xaa$^4$, Xaa$^5$, Cys, and R$^1$ of Formula (I). In the production method of the present invention, a compound represented by Formula (IV) is subjected to cyclization; therefore, the cyclic peptide compound or a pharmacologically acceptable salt thereof can be easily and efficiently produced.

The compound represented by Formula (IV) can be produced, for example, by using amino acids corresponding to Cys, Xaa$^1$, Xaa$^2$, Xaa$^3$, Xaa$^4$, Xaa$^5$, and Cys of Formula (IV), and a compound represented by Formula (V):

HOOC—(CH$_2$)$_n$—NH$_2$  (V), wherein n is the same as n of Formula (I), and by performing, for example, a chemical synthesis of peptide. Examples of the chemical synthesis include a solid-phase synthesis method, a stepwise extension method, a liquid-phase synthesis method, and the like. Of these chemical synthesis methods, a solid-phase synthesis method is preferable, because this method can easily produce the target cyclic peptide compound or a pharmacologically acceptable salt thereof in a high yield at a high purity. Examples of the solid-phase synthesis method include Fmoc and Boc synthesis, and the like. These solid-phase synthesis methods may be performed using a commercially available peptide synthesizer.

When a solid-phase synthesis method is employed, a resin for peptide synthesis, etc., can be used as the solid phase. Examples of the resin for peptide synthesis include PAM resin, chloromethyl resin, hydroxymethyl resin, benzhydrylamine resin, aminomethyl resin, 4-benzyloxybenzyl alcohol resin, 4-methylbenzhydrylamine resin, 4-hydroxymethylmethylphenyl acetamidomethyl resin, polyacrylamide resin, 4-(2',4'-dimethoxyphenyl-hydroxymethyl)phenoxy resin, and the like.

In a solid-phase synthesis method, the amino acids are used such that the intramolecular amino groups are protected in advance by protective groups. Examples of the protective groups include, but are not limited to, 9-fluorenyl-methoxycarbonyl (Fmoc) group, tert-butyloxycarbonyl (Boc) group, and the like. The amino acids may be used such that the side-chain functional groups are protected by protective groups that are suitable for the functional groups, as required. In this specification, an amino acid having protected amino group(s) and/or protected functional group(s) in the side chain is referred to as a "protected amino acid."

In Formula (V), when n is 1, glycine may be used as the compound represented by Formula (V). When n is 2 in Formula (V), β-alanine may be used as the compound represented by Formula (V). When n is 3 in Formula (V), 4-aminobutyric acid may be used as the compound represented by Formula (V). When n is an integer of 4 to 10 in Formula (V), the compound represented by Formula (V) may be obtained by chemical synthesis using the Strecker reaction. In a solid-phase synthesis method, the compound represented by Formula (V) is used such that the amino group(s) and, if necessary, the side-chain functional group(s) are protected by protective groups suitable for the functional group(s), as in the aforementioned case of the amino acids. In this specification, a compound represented by Formula (V) having protected amino group(s) or protected side-chain functional group(s) is referred to as a "protected compound."

When a solid-phase synthesis method is employed, the protected amino acids corresponding to Cys, Xaa$^5$, Xaa$^4$, Xaa$^3$, Xaa$^2$, Xaa$^1$, and Cys of Formula (IV) and protected compound corresponding to R$^1$ of Formula (IV) are sequentially condensed in the order of Cys, Xaa$^5$, Xaa$^4$, Xaa$^3$, Xaa$^2$, Xaa$^1$, R$^1$, and Cys on a resin for peptide synthesis. Thereafter, the product corresponding to the compound represented by Formula (IV) is cleaved from the resin for peptide synthesis; and at the same time, the protective groups are removed.

In the above-described condensation, an activation reagent, or the like, for use in general peptide synthesis is used. The reaction temperature in the condensation may be adjusted to a temperature that is usually employed in peptide synthesis. The reaction temperature is generally suitably selected from the range between about −20 to 50° C.

The protective groups may be removed, for example, by catalytic reduction in a hydrogen stream in the presence of a catalyst, acid treatment, alkali treatment, or the like.

After production of the compound represented by Formula (IV), the obtained product may be purified, if necessary. The purification may be performed, for example, by chromatography, such as reversed phase high-pressure liquid chromatography or ion-exchange chromatography.

Cyclization of the compound represented by Formula (IV) may be performed by oxidative crosslinking of the thiol groups of the cysteines at both ends of this compound. A disulfide between the cysteinyl groups may be formed, for example, by oxidizing the compound represented by Formula (IV) with iodine in an aqueous acid solution such as an aqueous acetic acid solution. Cyclization of the compound represented by Formula (IV) may also be performed by linking the cysteinyl groups at both ends of the compound through a peptide bond. The peptide bond may be formed by allowing a condensation reagent for use in general peptide synthesis to act on the compound represented by Formula (IV). As described above, the peptide compound of the present invention that has a cyclic structure and that is represented by Formula (I) can be prepared.

By using, for example, a protein sequencer, a mass spectrometer, or the like, the obtained product can be confirmed as the compound represented by Formula (I).

When the compound represented by Formula (I) is obtained as an educt, a pharmacologically acceptable salt of the compound represented by Formula (I) can be obtained by converting the obtained product into a pharmacologically acceptable salt by a known method, as required.

When the obtained product has the protective group in the molecule, the protective group may be removed by a known method. Introduction and deprotection of the protective group may also be performed in accordance with a method disclosed in Greene's Protective Groups in Organic Synthesis, 4th edition, Peter G. M. Wuts and Theodora W. Greene, 2006. The obtained product may be isolated and purified, if necessary. The isolation and purification of the product may be performed, for example, by chromatography, such as reversed phase high-pressure liquid chromatography or ion-exchange chromatography.

EXAMPLES

The present invention will be described in more detail below with reference to Examples. However, the present invention is not limited to these examples. It should be noted that hereinafter Cys denotes cysteinyl, Ser denotes seryl, Gln denotes glutaminyl, Glu denotes glutamyl, Ile denotes isoleucyl, and Gly denotes glycyl.

Production Example 1

Heat-inactivated fetal calf serum (FCS) was added to DMEM/HamF12 (produced by Sigma-Aldrich Corporation) to a concentration of 10 mass % to prepare a DMEM/HamF12 medium containing heat-inactivated FCS (hereinafter referred to as "DH10 medium").

Normal human epidermal keratinocyte HaCaT cells were cultured in the aforementioned DH10 medium at 37° C. in a 5 volume % carbon dioxide atmosphere.

DNA (SEQ ID NO: 6) encoding the T7 tag was added to the site corresponding to the N-terminus of epimorphin in cDNA encoding mouse epimorphin (GenBank Accession Number: E06629, SEQ ID NO: 5) to produce cDNA encoding T7-tagged epimorphin. The T7-tagged epimorphin-encoding cDNA was then inserted into an EcoRI recognition site of a retroviral expression vector pQCXIN (produced by Clontech) to produce an expression plasmid for T7-tagged epimorphin.

The obtained expression plasmid for T7-tagged epimorphin was introduced into packaging cells ("PT67 cells," produced by Clontech) using gene transfer reagents (trade names: "Lipofectamine" and "Plus Reagent," both produced by Invitrogen Corporation). Subsequently, culture supernatant was collected from the cells resistant to 500 µ/mL of geneticin (trade name: "G418," produced by Gibco Laboratories) among the obtained cells.

A retrovirus was obtained from the collected culture supernatant. The HaCaT cells were infected with the obtained retrovirus, and cultured in the presence of 500 µg/mL geneticin (trade name: "G418," produced by Gibco Laboratories) in a 5 volume % carbon dioxide atmosphere at 37° C. for 8 days. Thereafter, the expression of epimorphin in the cultured cells was investigated to thereby isolate keratinocytes producing T7-tagged epimorphin (HaCaT-TE cells).

Production Example 2

Fibroblast PT67 cells were cultured in DH10 medium in a 5 volume % carbon dioxide atmosphere at 37° C.

The expression plasmid for T7-tagged epimorphin obtained in Production Example 1 was introduced into PT67 cells using gene transfer reagents (trade names: "Lipofectamine" and "Plus Reagent," both produced by Invitrogen Corporation). The obtained cells were then cultured in the presence of 500 µg/mL geneticin (produced by Gibco Laboratories) in a 5 volume % carbon dioxide atmosphere at 37° C. for 8 days. Thereafter, the expression of epimorphin in the cultured cells was investigated to thereby isolate fibroblasts producing T7-tagged epimorphin (PT67-TE cells).

Production Example 3

A nucleic acid (SEQ ID NO: 7) encoding IL-2 signal peptide was added to the site corresponding to the N-terminus of epimorphin in cDNA (SEQ ID NO: 5) encoding epimorphin to obtain a nucleic acid encoding epimorphin bound to IL-2 signal peptide. The obtained nucleic acid was inserted into an EcoRI recognition site of a retroviral expression vector (produced by Clontech, trade name: "pQCXIN") to prepare an expression plasmid for cell surface epimorphin.

The obtained expression plasmid for cell surface epimorphin was introduced into packaging PT67 cells using Lipofectamine (trade name, produced by Invitrogen Corporation) and Plus Reagent (trade name, produced by Invitrogen Corporation). HaCaT cells were infected with a retrovirus obtained in the same manner as in Production Example 1. The obtained cells were then cultured in the presence of 500 µg/mL geneticin (trade name: G418, produced by Gibco Laboratories) in a 5 volume % carbon dioxide atmosphere at 37° C. for 8 days. Thereafter, the expression of epimorphin in the cultured cells was investigated to thereby isolate cells producing exogenous epimorphin (HaCaT-EPM cells).

Reference Example 1

HaCaT cells were cultured in a 5 volume % carbon dioxide atmosphere at 37° C. for 3 days in DH10 medium (Experiment No. 1), in DH10 medium containing 0.01 volume % oleic acid (Experiment No. 2), or in DH10 medium containing 0.025 volume % oleic acid (Experiment No. 3).

The cultured cells were isolated and the obtained cells were dissolved in a solubilizing reagent (composition: 2 volume % SDS, 10 volume % glycerol, 5 volume % 2-mercaptoethanol, 0.008 volume % bromophenol blue, and 0.65 M tris-HCl buffer (pH about 6.8)) to obtain a cell extract.

Western blotting was performed using the obtained cell extract and an anti-epimorphin antibody (produced by R & D Systems), and the relationship between oleic acid and the level of expression of endogenous epimorphin in HaCaT cells was investigated. The relationship between oleic acid and the level of expression of β-actin in HaCaT cells was also investigated in the same manner as above except that an anti-β-actin antibody was used in place of the anti-epimorphin antibody.

FIG. 1 shows the results of the relationship between the level of expression of endogenous epimorphin in HaCaT cells and oleic acid, investigated in Reference Example 1. In FIG. 1, Lane 1 shows a band corresponding to endogenous epimorphin obtained using the medium of Experiment No. 1. Lane 2 shows a band corresponding to endogenous epimorphin obtained using the medium of Experiment No. 2. Lane 3 shows a band corresponding to endogenous epimorphin obtained using the medium of Experiment No. 3.

The results shown in FIG. 1 indicate that the level of expression of endogenous epimorphin in HaCaT cells is similar regardless of the media used from Experiment Nos. 1 to 3; and that the level of expression of β-actin in HaCaT cells is also similar, regardless of the media used from Experiment Nos. 1 to 3. Therefore, these results indicate that oleic acid does not substantially affect the level of expression of endogenous epimorphin in HaCaT cells.

Reference Example 2

The HaCaT-TE cells obtained in Production Example 1 or the PT67-TE cells obtained in Production Example 2 were cultured in DH10 medium (Experiment No. 4), in DH10 medium containing 0.01 volume % oleic acid (Experiment No. 5), or in DH10 medium containing 0.025 volume % oleic acid (Experiment No. 6) in a 5 volume % carbon dioxide atmosphere at 37° C. for 3 days. The HaCaT-TE cells obtained in Production Example 1 or the PT67-TE cells obtained in Production Example 2 were irradiated with ultraviolet light B (UVB) at a dose of 10 mJ/cm$^2$, and then cultured in DH10 medium in a 5 volume % carbon dioxide atmosphere at 37° C. for 3 days (Experiment No. 7).

The obtained culture was centrifuged (at 1000×g for 30 minutes) to obtain a culture supernatant.

Using an anti-T7 tag antibody (produced by Novagen) and protein G Sepharose beads (produced by GE Healthcare), secreted epimorphin was collected from the obtained culture supernatant. The collected secreted epimorphin was subjected to Western blotting. Using an HRP-labeled anti-T7 tag antibody (produced by Novagen), the relationship between oleic acid and the amount of secreted epimorphin in each of the HaCaT-TE cell culture supernatant and the PT67-TE cell culture supernatant was investigated.

Figure 2:
[FIG. 2]
Figure 2:

FIG. 2 shows the relationship between oleic acid and the amount of secreted epimorphin in each of the HaCaT-TE cell culture supernatant and the PT67-TE culture supernatant, investigated in Reference Example 2. In FIG. 2, Lane 1 shows a band corresponding to secreted epimorphin obtained using the medium of Experiment No. 4. Lane 2 shows a band corresponding to secreted epimorphin obtained using the medium of Experiment No. 5. Lane 3 shows a band corresponding to secreted epimorphin obtained using the medium of Experiment No. 6. Lane 4 shows a band corresponding to secreted epimorphin obtained using the medium of Experiment No. 7.

The results shown in FIG. 2 indicate the following. When using the medium of Experiment No. 6 having the highest oleic acid concentration, the highest level of expression of secreted epimorphin in the keratinocyte HaCaT-TE cell culture supernatant was attained, which is similar to the level of expression of secreted epimorphin in the UVB-irradiated HaCaT-TE cell culture supernatant. On the other hand, when using the medium of Experiment No. 4 not containing oleic acid, the lowest level of expression of secreted epimorphin in the HaCaT-TE cell culture supernatant was attained. In contrast, in the case of the fibroblast PT67-TE cell culture supernatant, secreted epimorphin was not detected, regardless of the concentration of oleic acid. These results indicate that oleic acid induces secretion of epimorphin from keratinocytes, and thus suggest that skin parakeratosis caused by oleic acid is associated with abnormal skin conditions caused by epimorphin.

Example 1

A compound represented by Formula (I) wherein $Xaa^1$ is seryl, $Xaa^2$ is isoleucyl, $Xaa^3$ is glutamyl, $Xaa^4$ is glutaminyl, $Xaa^5$ is seryl, and n=1 was synthesized in the following manner.

(1) Synthesis of Peptide

As a starting material, an Fmoc-Cys(Trt)-Trt (2-Cl) resin (amount of Fmoc-Cys(Trt) per gram of 2-chlorotrityl chloride resin: 0.70 mmol) was placed in an amount corresponding to 0.25 mmol of Fmoc-Cys(Trt) in an automated peptide synthesizer (trade name: "430A," produced by Applied Biosystems).

First, under the control of the automatic peptide synthesizer program, 2 mmol of an Fmoc-amino acid derivative Fmoc-Ser(OBu) was activated with a coupling agent (dimethylformamide containing 0.45 M O-(benzotriazol-1-yl)-N,N,N',N'-tetramethyluronium hexafluorophosphate (hereinafter referred to as "HBTu") and 0.45 M 1-hydroxybenzotriazole (hereinafter referred to as "HOBt")), and placed into a reaction vessel to thereby perform a coupling reaction between the amino acid residue on the resin and the Fmoc-amino acid derivative in the reaction vessel, thus forming an Fmoc-protected peptide chain.

Subsequently, the Fmoc group in the Fmoc-protected peptide chain on the resin was removed (deprotected) using an N-methylpyrrolidone solution containing 20 volume % piperidine, and the resin containing the resulting peptide was washed. Thereafter, the above procedure was repeated using Fmoc-Gln(Trt), Fmoc-Glu(OBu), Fmoc-Ile, Fmoc-Ser (OBu), Fmoc-Gly, and Fmoc-Cys(Trt) in this order to thereby introduce the corresponding Fmoc-amino acid derivatives into the Fmoc-protected peptide chain on the resin according to the amino acid sequence of Cys-Gly-Ser-Ile-Glu-Gln-Ser-Cys (SEQ ID NO: 8). As a result, a resin containing an Fmoc group protecting peptide of the amino acid sequence (SEQ ID NO: 8) was obtained. The Kaiser test was performed, as appropriate, to confirm whether the coupling reaction was successfully completed.

The obtained Fmoc-protected peptide-containing resin was incubated in a mixture of trifluoroacetic acid (hereinafter referred to as "TFA"), triisopropylsilane (hereinafter referred to as "TIS"), water, and ethanedithiol (hereinafter referred to as "DT") (the TFA/TIS/water/DT ratio (by volume) is 92.5/2.5/2.5/2.5) at room temperature for 2 hours to deprotect the Fmoc group and cut off the peptide chain from the resin. After the incubation, 2-chlorotrityl chloride resin was separated from the mixture by filtration, and the obtained filtrate was concentrated under reduced pressure to distill off TFA from the filtrate. Cooled diethyl ether was added to the obtained residue to collect about 700 mg of a crude peptide as a precipitate.

About 700 mg of the obtained crude product was applied to a preparative high-performance liquid chromatograph(trade name: "Model LC8A," produced by Shimadzu Corporation) equipped with a reverse phase column (an octadecyl silica column with an inner diameter of 30 mm and a length of 250 mm, produced by Zorbax). Using a 0.1 volume % aqueous trifluoroacetic acid solution and a 0.1 volume % trifluoroacetic acid-containing acetonitrile solution, chromatography was performed at a flow rate of 1.0 mL/min for 25 minutes, while adjusting the acetonitrile concentration of the eluent to an acetonitrile concentration gradient of 1 to 60 volume % in the eluent. The fraction containing the desired peptide was collected, and acetonitrile was distilled off from the fraction. Subsequently, the residue was freeze-dried to obtain 110 mg of a trifluoroacetic acid salt of the desired peptide. The trifluoroacetic acid salt of the desired peptide was then desalinized to obtain the desired peptide (linear peptide). The results of the Kaiser test confirmed that the peptide comprises the amino acid sequence of Cys-Gly-Ser-Ile-Glu-Gln-Ser-Cys (SEQ ID NO: 8).

(2) Cyclization of the Peptide 110 mg (0.135 mmol) of the peptide obtained in (1) above was added to 130 mL of a 50 volume % acetic acid solution. Then, 210 µL (0.8 Eq) of a 0.5 M aqueous iodine solution was added to the obtained mixture, and mixed with stirring at room temperature for 3 hours. Thiol groups of two cysteinyl groups in the peptide were thereby oxidized to form a disulfide bond. Thereafter, 70 mg of ascorbic acid was added to the obtained mixture.

Subsequently, the obtained mixture was applied to a preparative HPLC (trade name: "Model LC8A," produced by Shimadzu Corporation) equipped with a reverse phase column (an octadecyl silica column with an inner diameter of 30 mm and a length of 250 mm, produced by Zorbax). While adjusting the acetonitrile concentration of the eluent to an acetonitrile concentration gradient of 1 to 60 volume % in the eluent using a 0.1 volume % aqueous trifluoroacetic acid solution and a 0.1 volume % trifluoroacetic acid-containing acetonitrile solution, chromatography was performed at a flow rate of 1.0 mL/min for 25 minutes. As a result, 20 mg of a product was obtained.

(3) Confirmation of the Cyclic Peptide Compound

Figure 3:
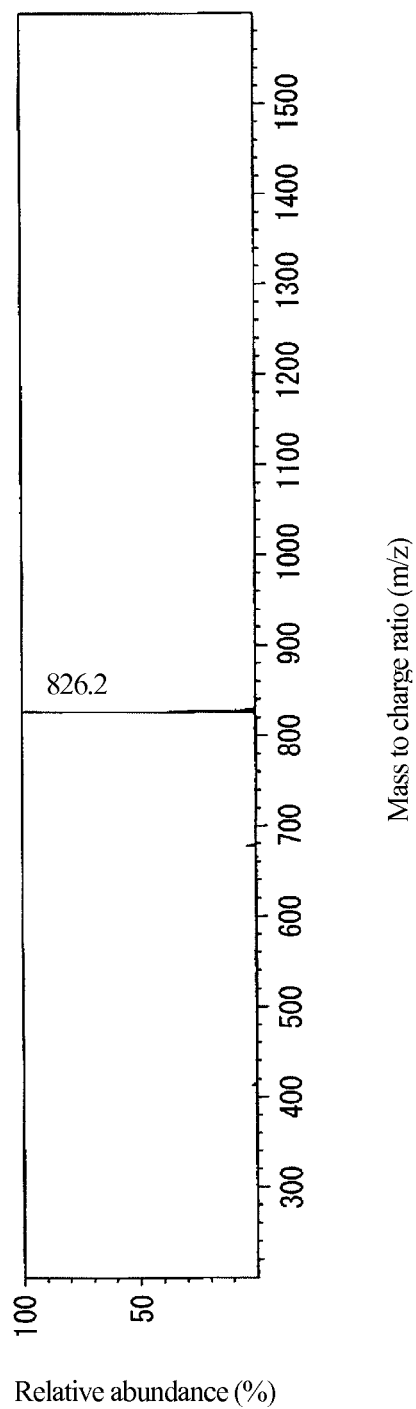
[FIG. 3]
Figure 4:
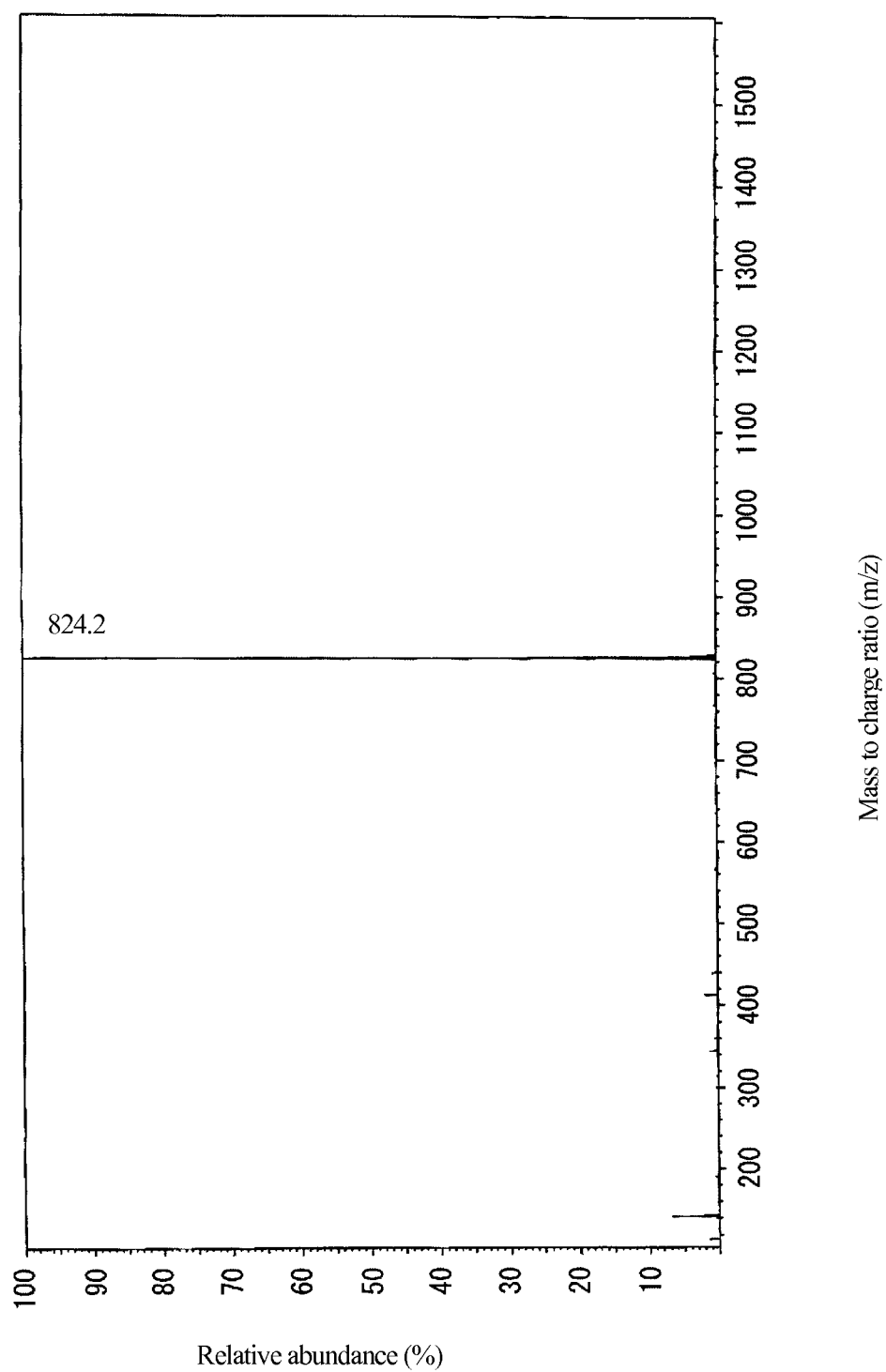
[FIG. 4]

The peptide obtained in (1) above and the peptide obtained in (2) above (oxidized peptide) were each subjected to a mass spectrometer (trade name: "LC-MS-2010," produced by Shimadzu Corporation) to determine the mass spectra of the peptide obtained in (1) above and the oxidized peptide obtained in (2) above. FIG. 3 shows the mass spectrum of the peptide obtained in Example 1. FIG. 4 shows the mass spectrum of the oxidized peptide obtained in Example 1.

The results shown in FIG. 3 indicate that in the mass spectrum of the peptide obtained in (1) above, a peak was found at 826.2 m/z, which is close to the theoretical value of the peptide of the amino acid sequence of Cys-Gly-Ser-Ile-Glu-Gln-Ser-Cys (SEQ ID NO: 8). This result proved that the peptide obtained in (1) above consists of the amino acid sequence of Cys-Gly-Ser-Ile-Glu-Gln-Ser-Cys (SEQ ID NO: 8).

The results shown in FIGS. 3 and 4 indicate that a peak is found at 826.2 m/z in the mass spectrum of the peptide obtained in (1) above (see FIG. 3), whereas a peak is found at 824.2 m/z, which corresponds to two hydrogen atoms less than 826.2 m/z, in the mass spectrum of the oxidized peptide obtained in (2) above (FIG. 4). These results confirmed that the oxidized peptide obtained in (2) above was formed by cyclization of the peptide obtained in (1) above through a disulfide bond between two cysteinyl groups. It was thus found that the oxidized peptide obtained in (2) above is a cyclic peptide compound represented by Formula (I) wherein $Xaa^1$ is seryl, $Xaa^2$ is isoleucyl, $Xaa^3$ is glutamyl, $Xaa^4$ is glutaminyl, $Xaa^5$ is seryl, $R^1$ is a group represented by Formula (III), and n is 1. The purity of the cyclic peptide compound as confirmed by HPLC was 98.2%.

Example 2

A cyclic peptide compound was produced in the same manner as in Example 1, except that a compound wherein n=5 was used in place of the compound wherein n=1.

Example 3

A cyclic peptide compound was produced in the same manner as in Example 1, except that a compound wherein n=8 was used in place of the compound wherein n=1.

Comparative Example 1

The same procedure as in Example 1 (1) was repeated, except that a Fmoc-Asp(OBu)-Alko-resin (the amount of Fmoc-Asp(OBu) per gram of the resin: 0.70 mmol) was used in an amount corresponding to 0.25 mmol of Fmoc-Asp (OBu) in place of the Fmoc-Cys(Trt)-Trt(2-Cl) resin; and that Fmoc-Gln(Trt), Fmoc-Glu(OBu), Fmoc-Ile, and Fmoc-Ser (OBu) were used in this order as Fmoc-amino acid derivatives in place of Fmoc-Ser(OBu), Fmoc-Gln(Trt), Fmoc-Glu (OBu), Fmoc-Ile, Fmoc-Ser(OBu), Fmoc-Gly, and Fmoc-Cys(Trt) in this order. As a result, a linear peptide consisting of the amino acid sequence of Ser-Ile-Glu-Gln-Ser-Cys-Asp (SEQ ID NO: 3) was obtained.

Test Example 1

The cyclic peptide compound obtained in Example 1 was added to purified water to a concentration of 10 µg/mL to obtain a sample. The obtained sample was then added to DH10 medium in such an amount as to achieve a concentration of the cyclic peptide compound obtained in Example 1 of 0.001 mass %. The HaCaT-EPM cells obtained in Production Example 3 were cultured in the obtained medium at 37° C. in a 5 volume % carbon dioxide atmosphere, and the cells were collected over time. After adding 110 µL of a mixture of solution B with reagent A (trade name: "WST-1, " produced by Dojindo) (the reagent A/Solution B ratio by volume=10/1) provided with a cell counter kit (trade name: "Cell Counting Kit," produced by Dojindo), the collected cells were incubated for 3 hours. The absorbance of the obtained mixture at 450 nm was measured using a spectrophotometer (trade name: "ARVOtmS X 1420 Multilabel Counter," produced by Wallac), and the effect of the mixture on the HaCaT-EPM cell growth was investigated. As a control, the above procedure was repeated, except that purified water was used in place of the cyclic peptide compound obtained in Example 1, and the effect on the growth of HaCaT-EPM cells was investigated.

Further, the above procedure was repeated except that the cyclic peptide compound obtained in Example 2, the cyclic peptide compound obtained in Example 3, or the linear peptide obtained in Comparative Example 1 was used in place of the cyclic peptide compound obtained in Example 1; and the effects on the growth of HaCaT-EPM cells were investigated. Table 1 shows the effects on the growth of HaCaT-EPM cells by the cyclic peptide compound obtained in Example 1, the cyclic peptide compound obtained in Example 2, the cyclic peptide compound obtained in Example 3, and linear peptide obtained in Comparative Example 1. The scoring criteria in Table 1 are as follows:

++: Compared to the case of using the control, significant growth recovery of HaCaT-EPM cells was detected ($P \leq 0.01$).

+: Compared to the case of using the control, significant growth recovery of HaCaT-EPM cells was detected (P≤0.05).
−: Significant growth recovery of HaCaT-EPM cells was not detected.

TABLE 1

|  | N | Score |
| --- | --- | --- |
| Example 1 | 1 | ++ |
| Example 2 | 5 | + |
| Example 3 | 8 | + |
| Comparative Example 1 | − | − |

The results shown in Table 1 indicate the following. HaCaT-EPM cells cultured in the media containing the cyclic peptide compounds obtained in Examples 1 to 3 grew well. In particular, the HaCaT-EPM cells cultured in the medium containing the cyclic peptide compound obtained in Example 1 grew well. In contrast, the HaCaT-EPM cells cultured in the medium containing the cyclic peptide compound obtained in Comparative Example 1 grew poorly. When epimorphin was expressed in HaCaT cells, the cells grew poorly. These results suggest that the cyclic peptide compounds obtained in Examples 1 to 3 suppress the physiological activity of epimorphin, and thus improve cell growth.

Production Example 4

The cyclic peptide compound obtained in Example 1 was dissolved in purified water to a concentration of 10 μg/mL. Test Sample 1 was thus obtained. The linear peptide obtained in Comparative Example 1 was dissolved in purified water to a concentration of 10 μg/mL. Test Sample 2 was thus obtained.

Test Example 2

In the following experiment, DH10 was used as a medium of Experimental No. 8. A 1 volume % oleic acid-containing ethanol solution was added to DH10 in such a manner that oleic acid had a concentration of 0.05 volume % to obtain a medium (Experimental No. 9). Further, a 1 volume % oleic acid-containing ethanol solution and Test Sample 2 obtained in Production Example 4 were added to DH10 in such a manner that oleic acid had a concentration of 0.05 volume % and a linear peptide had a concentration of 0.0001 mass % to obtain a medium (Experimental No. 10). Alternatively, a 1 volume % oleic acid-containing ethanol solution and Test Sample 1 obtained in Production Example 4 were added to DH10 in such a manner that oleic acid had a concentration of 0.05 volume % and a cyclic peptide compound had a concentration of 0.0001 mass % to obtain a medium (Experimental No. 11).

HaCaT cells were cultured in the DH10 medium at 37° C. in a 5 volume % carbon dioxide atmosphere.

Next, the obtained HaCaT cells were suspended in 350 μL of DH10 medium containing 1000 U/mL DNase I (produced by Sigma Aldrich Co.). While rotating the obtained suspended solids in a 24-well dish (produced by Corning Inc., super-low adhesion surface) at 100 min$^{-1}$, gyratory culturing was performed for 24 hours at 37° C. in a 5 volume % carbon dioxide atmosphere to form a smooth, round cell aggregate.

The formed cell aggregate was embedded in a high-density collagen gel prepared with a 0.5 mass % collagen solution (type IA) (produced by Koken Co., Ltd.).

Next, the cell aggregate after embedding was cultured for 4 days in a 5 volume % carbon dioxide atmosphere at 37° C. in the medium of Experimental Nos. 8, 9, 10, or 11 to form a cell cluster. The morphology of the obtained cell cluster was observed by a phase-contrast microscope.

In the cell cluster, the outermost layer cells maintain the undifferentiated state because they are in contact with collagen; however, in general, cells that are located inside the undifferentiated cells of the outermost layer promptly start differentiation, and undergo anoikis. Therefore, in the cell cluster, luminal space that can be easily recognized is formed 3 to 4 days after the beginning of culturing under normal conditions. 100 randomly selected cell clusters were observed, and the lumen formation rate was calculated by measuring the ratio of cell clusters in which obvious lumen formation was observed to 100 cell clusters in total.

Figure 5:
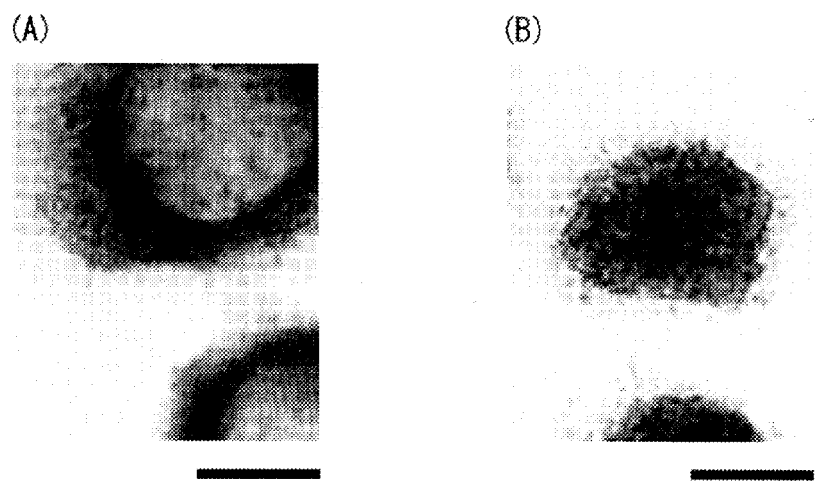
[FIG. 5] FIG. 5 (A) is a photograph serving as a drawing and showing the morphology of the cell cluster in which the medium of Experimental No. 11 was used in Test Example 2.

FIG. 5 (A) shows the results obtained by observing the morphology of the cell cluster when the medium of Experimental No. 11 was used in Test Example 2. FIG. 5 (B) shows the results obtained by observing the morphology of the cell cluster when the medium of Experimental No. 10 was used in Test Example 2. In the figure, the scale bar shows a length of 100 μm.

Figure 6:
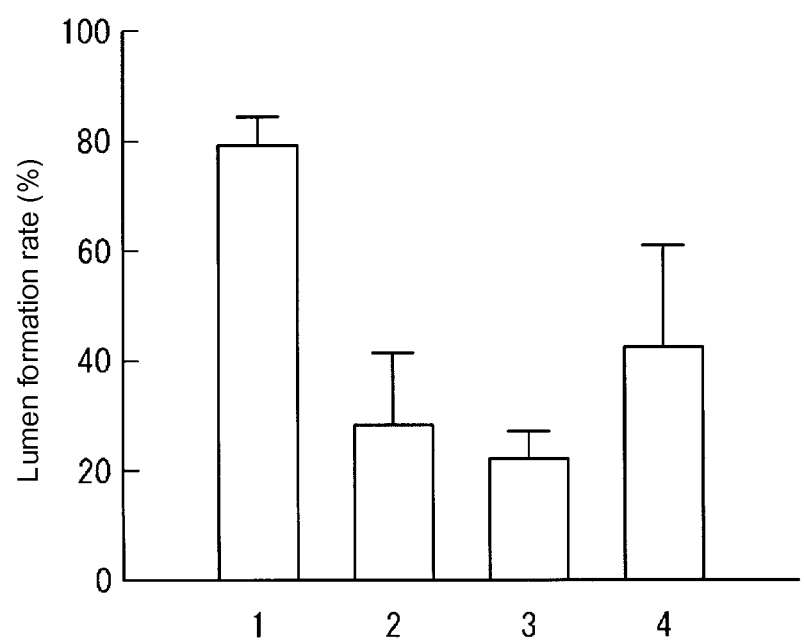
[FIG. 6]

FIG. 6 shows the results obtained by examining the relationship between the kind of medium and the lumen formation rate in Test Example 2. In the figure, lane 1 shows a lumen formation rate in cell clusters when the medium of Experimental No. 8 was used, lane 2 shows a lumen formation rate in cell clusters when the medium of Experimental No. 9 was used, lane 3 shows a lumen formation rate in cell clusters when the medium of Experimental No. 10 was used, and lane 4 shows a lumen formation rate in cell clusters when the medium of Experimental No. 11 was used.

The results shown in FIGS. 5 (A) and (B), and FIG. 6 indicate that the cell clusters obtained when the medium of Experimental No. 11 was used had a high lumen formation rate; however, that the cell clusters obtained when the medium of Experimental No. 10 was used had a low lumen formation rate. The results indicate that although the cyclic peptide compound obtained in Example 1 inhibits the generation of abnormal lumen formation in cell clusters caused by oleic acid, the linear peptide obtained in Comparative Example 1 does not inhibit the generation of abnormal lumen formation in cell clusters caused by oleic acid. The lumen formation in the cell clusters reflects the differentiation and conditions in the skin. Accordingly, it is suggested that the cyclic peptide compound obtained in Example 1 can inhibit the generation of abnormalities in skin conditions caused by oleic acid.

Test Example 3

(1) Preparation of Medium

In the following experiment, DH10 medium was used as the medium of Experimental No. 12. 1 μL of purified water was added to 1 mL of DH10 medium to obtain a medium (Experimental No. 13). Further, Test Sample 2 obtained in Production Example 4 was added to DH10 medium in such a manner that a linear peptide had a concentration of 0.0001 mass % to obtain a medium (Experimental No. 14). Alternatively, Test Sample 1 obtained in Production Example 4 was added to DH10 medium in such a manner that a cyclic peptide compound had a concentration of 0.0001 mass % to obtain a medium (Experimental No. 15).

(2) Formation of Cell Cluster (Cell Construct) and Calculation of Lumen Formation Rate Except for using the HaCaT-EPM cells obtained in Production Example 3 in place of the HaCaT cells in Test Example 2, and the medium of Experimental No. 12, 13, 14, or 15 in place of the medium of Experimental No. 8, 9, 10, or 11 in Test Example 2, the same procedure as in Test Example 2 was performed to calculate a lumen formation rate.

Figure 7:
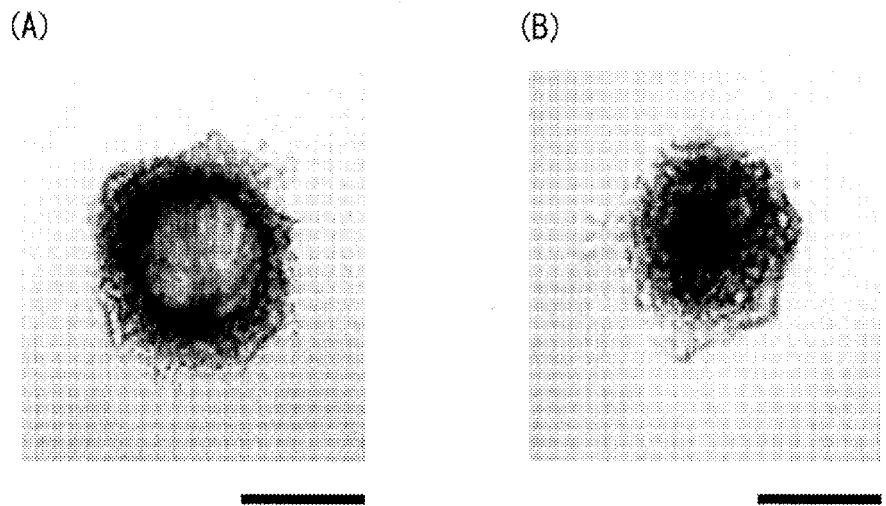
[FIG. 7] FIG. 7 (A) is a photograph serving as a drawing and showing the morphology of the cell cluster in which the medium of Experimental No. 15 is used in Test Example 3.

FIG. 7 (A) shows the results obtained by observing the morphology of the cell cluster when the medium of Experimental No. 15 was used in Test Example 3. FIG. 7 (B) shows the results obtained by observing the morphology of the cell cluster when the medium of Experimental No. 14 was used in Test Example 3. In the figure, the scale bar shows a length of 100 µm.

Figure 8:
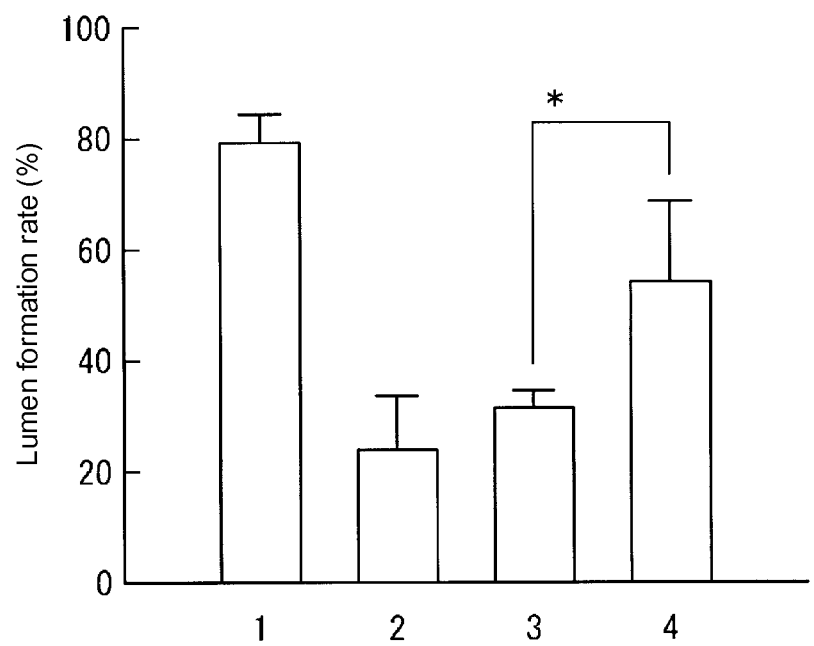
[FIG. 8]

FIG. 8 shows the results obtained by examining the relationship between the kind of medium and the lumen formation rate in Test Example 3. In the figure, lane 1 shows a lumen formation rate in cell clusters when the medium of Experimental No. 12 was used, lane 2 shows a lumen formation rate in cell clusters when the medium of Experimental No. 13 was used, lane 3 shows a lumen formation rate in cell clusters when the medium of Experimental No. 14 was used, and lane 4 shows a lumen formation rate in cell clusters when the medium of Experimental No. 15 was used. In the figure, data is based on three counts, and expressed by average ± standard deviation. In the figure, * represents P<0.05.

The results shown in FIGS. 7 (A) and (B) and FIG. 8 indicate that the cell clusters obtained when the medium of Experimental No. 15 was used had a high lumen formation rate; however, that the cell clusters obtained when the medium of Experimental No. 14 was used had a low lumen formation rate. The results indicate that although the cyclic peptide compound obtained in Example 1 inhibits the generation of abnormal lumen formation in cell clusters caused by epimorphin, the linear peptide obtained in Comparative Example 1 does not inhibit the generation of abnormal lumen formation in cell clusters caused by epimorphin. Accordingly, it is suggested that the cyclic peptide compound obtained in Example 1 can inhibit the generation of abnormalities in skin conditions caused by epimorphin.

Test Example 4

(1) Preparation of Medium

In the following experiment, DH10 medium was used as a medium of Experimental No. 16. A 1 volume % oleic acid-containing ethanol solution was added to DH10 medium in such a manner that oleic acid had a concentration of 0.02 volume % to obtain a medium (Experimental No. 17). Further, a 1 volume % oleic acid-containing ethanol solution and Test Sample 2 obtained in Production Example 4 were added to DH10 medium in such a manner that oleic acid had a concentration of 0.02 volume % and a linear peptide had a concentration of 0.000001 mass % to obtain a medium (Experimental No. 18). Alternatively, a 1 volume % oleic acid-containing ethanol solution and Test Sample 1 obtained in Production Example 4 were added to DH10 medium in such a manner that oleic acid had a concentration of 0.02 volume % and a cyclic peptide compound had a concentration of 0.000001 mass % to obtain a medium (Experimental No. 19). A 1 volume % oleic acid-containing ethanol solution and Test Sample 2 obtained in Production Example 4 were added to DH10 medium in such a manner that oleic acid had a concentration of 0.02 volume % and a linear peptide had a concentration of 0.00001 mass % to obtain a medium (Experimental No. 20). A 1 volume % oleic acid-containing ethanol solution and Test Sample 1 obtained in Production Example 4 were added to DH10 medium in such a manner that oleic acid had a concentration of 0.02 volume % and a cyclic peptide had a concentration of 0.00001 mass % to obtain a medium (Experimental No. 21). A 1 volume % oleic acid-containing ethanol solution and Test Sample 2 obtained in Production Example 4 were added to DH10 medium in such a manner that oleic acid had a concentration of 0.02 volume % and a linear peptide had a concentration of 0.0001 mass % to obtain a medium (Experimental No. 22). A 1 volume % oleic acid-containing ethanol solution and Test Sample 1 obtained in Production Example 4 were added to DH10 medium in such a manner that oleic acid had a concentration of 0.02 volume % and a cyclic peptide had a concentration of 0.0001 mass % to obtain a medium (Experimental No. 23).

(2) Calculation of Cornified Envelope Formation Rate

HaCaT cells were cultured for 3 days in a medium of any one of Experimental Nos. 16 to 23 at 37° C. in a 5 volume % carbon dioxide atmosphere.

Next, the obtained HaCaT cells were washed with phosphate buffered saline, and incubation was performed in 500 µL of a trypsin EDTA solution (produced by Sigma Corporation) at 37° C. for 3 minutes.

Thereafter, the obtained HaCaT cells were suspended in a serum-free DH medium (DMEM/HamF12, produced by Sigma Aldrich) to $1.0 \times 10^5$ cell/mL. Calcium ionophore A23187 (produced by Sigma Aldrich), which causes calcium influx, was added to the obtained suspension in such a manner that the mixture had a concentration of 20 ng/mL, and the HaCaT cells contained in the obtained mixture were cultured in a 5 volume % carbon dioxide atmosphere at 37° C. for 5 hours.

The obtained cells were washed with phosphate buffered saline. The cells after washing were subjected to incubation for 10 minutes in a solubilized liquid (composition: 2 mass % SDS, 20 mM dithiothreitol, and residual purified water). Thereafter, the number of residual insoluble cells resulting from an insoluble cornified envelope after the entry of calcium ionophore A23187 was calculated by an optical microscope. The cornified envelope formation rate was calculated using the number of cells in total and the number of residual insoluble cells.

Figure 9:
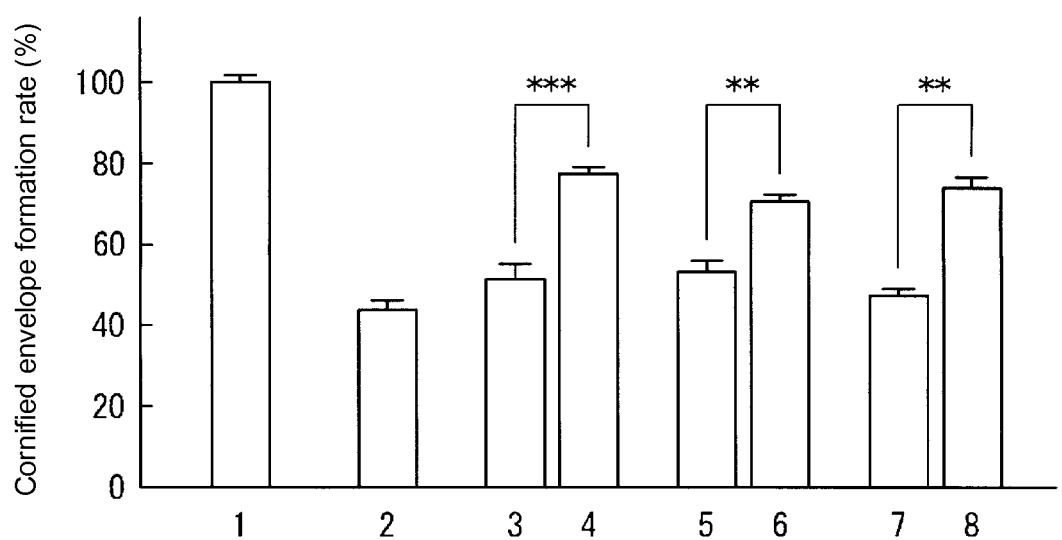
[FIG. 9]

FIG. 9 shows the results obtained by examining the relationship between the kind of medium and the cornified envelope formation rate in Test Example 4. In the figure, lane 1 shows a cornified envelope formation rate in Experimental No. 16, lane 2 shows a cornified envelope formation rate in Experimental No. 17, lane 3 shows a cornified envelope formation rate in Experimental No. 18, lane 4 shows a cornified formation rate in Experimental No. 19, lane 5 shows a cornified formation rate in Experimental No. 20, lane 6 shows a cornified formation rate in Experimental No. 21, lane 7 shows a cornified formation rate in Experimental No. 22, and lane 8 shows a cornified formation rate in Experimental No. 23. In the figure, the data is based on three counts, and expressed by average ± standard deviation. In the figure,  represents P<0.01, and * represents P<0.001.

The results shown in FIG. 9 indicate that the cornified envelope formation rate (Experimental No. 19 (4 in FIG. 9), 21 (6 in FIG. 9) and 23 (8 in FIG. 9) obtained when the medium containing the cyclic peptide compound obtained in Example 1 was used was higher than the cornified envelope formation rate (Experimental No. 18 (3 in FIG. 9), 20 (5 in FIG. 9) and 22 (7 in FIG. 9) obtained when the medium containing the linear peptide compound obtained in Comparative Example 1 was used. The cornified envelope formation rate reflects the differentiated state in the skin. Accordingly, the results suggested that the cyclic peptide compound obtained in Example 1 can inhibit the generation of abnormalities in skin conditions caused by oleic acid.

Test Example 5

(1) Preparation of Medium

In the following experiment, DH10 medium was used as a medium of Experimental No. 24 or 25. Test sample 2 obtained in Production Example 4 was added to DH10 medium in such a manner that linear peptide had a concentration of 0.000001 mass % to obtain a medium (Experimental No. 26). Alternatively, Test Sample 1 obtained in Production Example 4 was added to DH10 medium in such a manner that a cyclic peptide compound had a concentration of 0.000001 mass % to obtain a medium (Experimental No. 27). Test sample 2 obtained in Production Example 4 was added to DH10 medium in such a manner that linear peptide had a concentration of 0.00001 mass % to obtain a medium (Experimental No. 28). Test sample 1 obtained in Production Example 4 was added to DH10 medium in such a manner that a cyclic peptide compound had a concentration of 0.00001 mass % to obtain a medium (Experimental No. 29). Test sample 2 obtained in Production Example 4 was added to DH10 medium in such a manner that linear peptide had a concentration of 0.0001 mass % (Experimental No. 30). Test sample 1 obtained in Production Example 4 was added to DH10 medium in such a manner that a cyclic peptide compound had a concentration of 0.0001 mass % to obtain a medium (Experimental No. 31).

(2) Calculation of Cornified Envelope Formation Rate

HaCaT cells were cultured for 3 days in the medium of Experimental No. 24 at 37° C. in a 5 volume % carbon dioxide atmosphere.

When HaCaT-EPM cells were used, it was cultured for 3 days in a medium of any one of Experimental Nos. 25 to 31 at 37° C. in a 5 volume % carbon dioxide atmosphere.

Next, the obtained HaCaT cells or HaCaT-EPM cells were washed with phosphate buffered saline, and incubation was performed in 500 μL of a trypsin EDTA solution at 37° C. for 3 minutes.

Thereafter, the obtained HaCaT cells or HaCaT-EPM cells were suspended in a serum-free DH medium to $1.0 \times 10^5$ cell/mL. Calcium ionophore A23187, which causes calcium influx, was added to the obtained suspension in such a manner that the concentration thereof is 20 ng/mL, and the HaCaT cells contained in the obtained mixture were cultured in a 5 volume % carbon dioxide atmosphere at 37° C. for 5 hours.

The cornified envelope formation rate was calculated by performing the same procedure as in Test Example 4.

Figure 10:
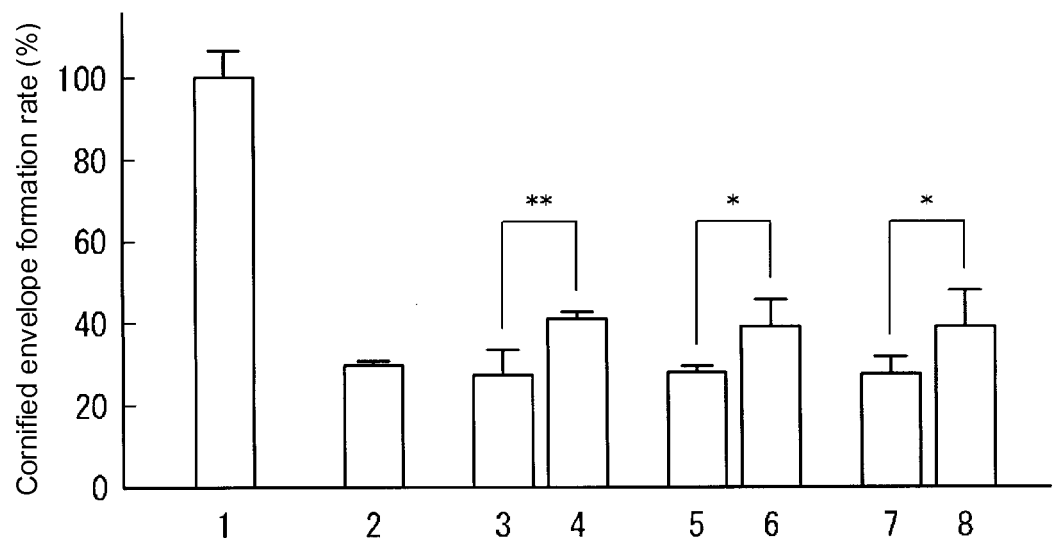
[FIG. 10]

FIG. 10 shows the results obtained by examining the relationship between the kind of medium or cell and the cornified envelope formation rate in Test Example 5. In the figure, 1 shows a cornified envelope formation rate in Experimental No. 24, 2 shows a cornified envelope formation rate in Experimental No. 25, 3 shows a cornified envelope formation rate in Experimental No. 26, 4 shows a cornified formation rate in Experimental No. 27, 5 shows a cornified formation rate in Experimental No. 28, 6 shows a cornified formation rate in Experimental No. 29, 7 shows a cornified formation rate in Experimental No. 30, and 8 shows a cornified formation rate in Experimental No. 31. In the figure, the data is based on three counts, and expressed by average ± standard deviation. In the figure, * represents $P<0.05$, and ** represents $P<0.01$.

The results shown in FIG. 10 indicate that the cornified envelope formation rate (Experimental No: 27 (4 in FIG. 10), 29 (6 in FIG. 10), and 31 (8 in FIG. 10)) in which the medium containing the cyclic peptide compound obtained in Example 1 was used was higher than the cornified envelope formation rate (Experimental No: 26 (3 in FIG. 10), 28 (5 in FIG. 10) and 30 (7 in FIG. 10)) in which the medium containing the linear peptide obtained in Comparative Example 1 was used. Accordingly, the results suggest that the cyclic peptide compound obtained in Example 1 can inhibit the generation of abnormalities in skin conditions caused by epimorphin.

Test Example 6

(1) Preparation of Sample

In the following experiment, a 50 volume % ethanol aqueous solution was used as a sample of Experimental No. 32 or 33. The cyclic peptide compound obtained in Example 1 was added to the 50 volume % ethanol aqueous solution so that the cyclic peptide compound had a concentration of 10 ng/mL to obtain a sample (Experimental No. 35).

The linear peptide obtained in Comparative Example 1 was added to the 50 volume % ethanol aqueous solution in such a manner that the linear peptide had a concentration of 10 ng/mL to obtain a sample (Experimental No. 34).

(2) Evaluation of Sample

100 μL of a sample of any one of Experimental Nos. 32 to 35 was applied to the back skin of a female 7-year-old hairless mouse Hos/hr-1 (hereinbelow, referred to as "Hos/hr-1 mouse," provided by SLC Inc.) on the first day and the third day after beginning of feeding, and fed for two days.

Thereafter, regarding Experimental No. 32, 100 μL of the sample was applied to the application site of the Hos/hr-1 mouse twice a day over 3 days, after which 100 μL of ethanol was applied thereto, and 100 μL of the sample was applied again thereto.

Regarding Experimental Nos. 33 to 35, 100 μL of the sample of any one of Experimental Nos. 33 to 35 was applied to the application site of the Hos/hr-1 mouse twice a day over 3 days, after which 100 μL of a 10 volume % oleic acid-containing ethanol solution was applied, and 100 μL of the sample of any one of Experimental Nos. 33 to 35 was applied again thereto.

Thereafter, the Hos/hr-1 mouse was fed for one another day.

On the 8th day after the beginning of the first application of a sample of any one of Experimental Nos. 32 to 35, a skin structure was extracted from the application site. From the extracted skin structure, the frozen section was prepared. The cell nucleus of the frozen section was dyed blue-purple by hematoxylin-eosin, and most of the cytoplasm substance was dyed red to measure the epidermal thickness.

Figure 11:
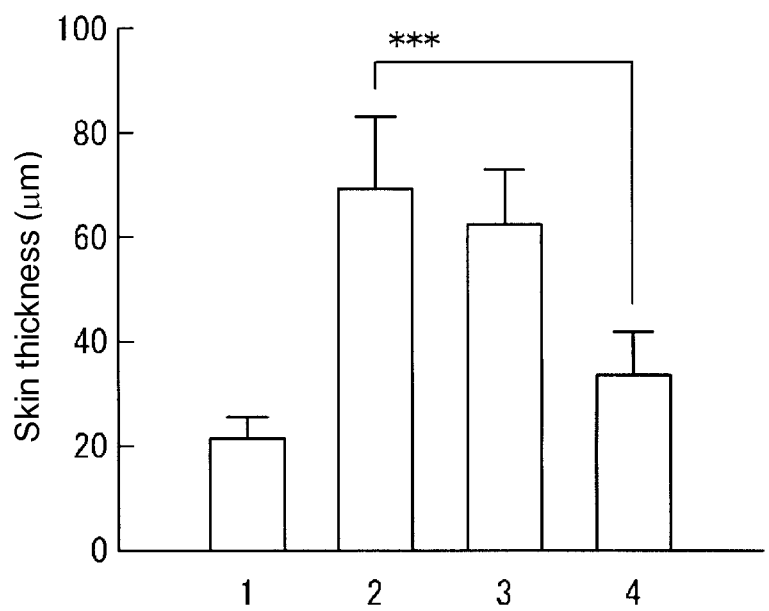
[FIG. 11]

FIG. 11 shows the results obtained by examining the relationship between the kind of sample and the epidermal thickness in Test Example 6. In the figure, 1 shows an epidermal thickness when the sample of Experimental No. 32 was used, 2 shows an epidermal thickness when the sample of Experimental No. 33 was used, 3 shows an epidermal thickness when the sample of Experimental No. 34 was used, and 4 shows an epidermal thickness when the sample of Experimental No. 35 was used. In the figure, the data is based on ten counts, and expressed by average ± standard deviation. In the figure, *** represents $P<0.001$.

Further, the horny layer was extracted by applying an adhesive tape (produced by Sumitomo 3M Co., Ltd.) to the aforementioned application site. The nucleus of the extracted horny layer was dyed by propidium iodide (produced by Sigma Aldrich).

Figure 12:
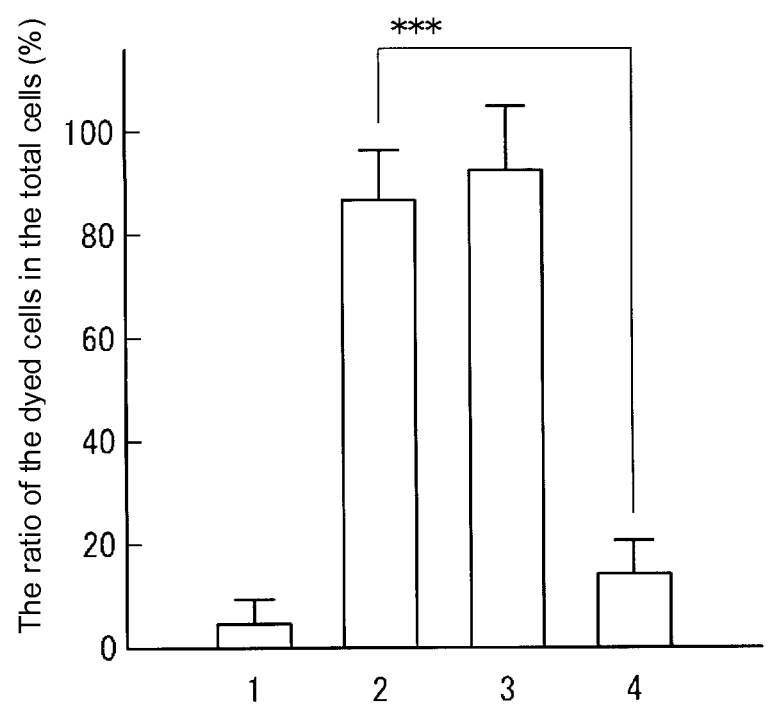
[FIG. 12]

FIG. 12 shows the results obtained by examining the relationship between the kind of sample and the ratio of the dyed cells in the total cells in Test Example 6. In the figure, 1 shows a ratio of the dyed cells in the total cells when the sample of Experimental No. 32 was used, 2 shows a ratio of the dyed cells in the total cells when the sample of Experimental No. 33 was used, 3 shows a ratio of the dyed cells in the total cells when the sample of Experimental No. 34 was used, and 4 shows a ratio of the dyed cells in the total cells when the sample of Experimental No. 35 was used. In the figure, the data is based on three counts, and expressed by average ± standard deviation. In the figure, *** represents P<0.001.

The results shown in FIG. 11 indicate that the epidermal thickness obtained using the sample of Experimental No. 35 that contains the cyclic peptide compound of Example 1 was thinner than the epidermal thickness obtained using the sample of Experimental No. 34 that contains the linear peptide obtained in Comparative Example 1. Further, the results shown in FIG. 12 indicate that the ratio of the dyed cells in the total cells in which the sample of Experimental No. 35 that contains the cyclic peptide compound obtained in Example 1 was used was significantly smaller than the ratio of the dyed cells in the total cells in which the sample of Experimental No. 34 that contains the linear peptide obtained in Comparative Example 1 was used. Therefore, the results suggests that the cyclic peptide compound obtained in Example 1 can inhibit the generation of abnormalities in skin conditions caused by oleic acid.

Test Example 7

In the following experiment, DH10 medium was used as a medium of Experimental No. 36. 1 μL of purified water was added to 1 mL of DH10 medium to obtain a sample (Experimental No. 37). Further, the cyclic peptide compound obtained in Example 1 was added to DH10 medium to a concentration of 0.001 mass % to obtain a sample (Experimental No. 38). Furthermore, the linear peptide obtained in Comparative Example 1 was added to DH10 medium to a concentration of 0.001 mass %, to obtain a sample (Experimental No. 39).

MRC-5 cells, which are human fetal lung fibroblast cells, were cultured in 10 mL of α-MEM (produced by Gibco Laboratories containing 10 mass % heat inactivated FCS at 37° C. in a 5 volume % carbon dioxide atmosphere for 72 hours.

A support (produced by BD Bioscience Co., Ltd.; trade name: cell culture insert) was provided in each well of a 24 well culture plate. In the support, the MRC-5 cells and a collagen gel mixed solution (collagen type I, produced by Nitta Gelatin, Inc.) were mixed. The obtained mixture was formed into a gel to obtain a cell-embedded gel ($1.7 \times 10^5$/ mL). 0.05 ml of a 1 mg/mL fibronectin aqueous solution (produced by BD Biosciences was added to the upper surface of the obtained cell-embedded gel, and the cell-embedded gel was allowed to stand for 1 hour at room temperature. Next, the MRC-5 cells in the cell-embedded gel were subjected to incubation in DH10 medium at 37° C. overnight in a 5 volume % carbon dioxide atmosphere.

Thereafter, HaCaT cells ($7.0 \times 10^4$ cells) that had been suspended in 0.2 mL of DH10 medium containing hydrocortisone (0.4 μg/mL, produced by Sigma Aldrich), gentamycin (100 μg/mL, produced by Gibco Laboratories), insulin (5 μg/(ml)), and ascorbic acid (50 μg/mL, made by Sigma Aldrich) were scattered on the cell-embedded gel.

Next, the cell-embedded gel in which the HaCaT cells were scattered was immersed in DH10 in a well of the 24-well culture plate. Thereafter, the cells contained in the cell-embedded gel were subjected to incubation in a 5 volume % carbon dioxide atmosphere at 37° C. for 5 days to obtain a cellular architecture. Next, the surface of the HaCaT cells in the obtained cellular architecture was raised to the contact surface between the air and the DH10, and the cellular architecture was cultured for 15 days at 37° C. in a 5 volume % carbon dioxide atmosphere to obtain a differentiated cellular architecture containing HaCaT cells.

Thereafter, regarding Experimental No. 36, 5 μL of the sample of Experimental No. 36 was applied to the surface of a differentiated cellular architecture, and the differentiated cellular architecture was cultured for one day at 37° C. in a 5 volume % carbon dioxide atmosphere. On the other hand, regarding Experimental Nos. 37 to 39, 5 μL of a 0.5 volume % oleic acid-containing ethanol solution and 5 μL of the sample of any one of Experimental Nos. 37 to 39 were applied to the surface of the differentiated cellular architecture, and the differentiated cellular architecture was cultured at 37° C. for one more day in a 5 volume % carbon dioxide atmosphere.

From the obtained cell construct, the frozen section was prepared. The cell nucleus of the frozen section was dyed blue-purple by hematoxylin-eosin, and most of the cytoplasm substance was dyed red. Using the frozen section after dyeing, the tissue morphology of the cell construct was observed by a phase microscope.

Figure 13:
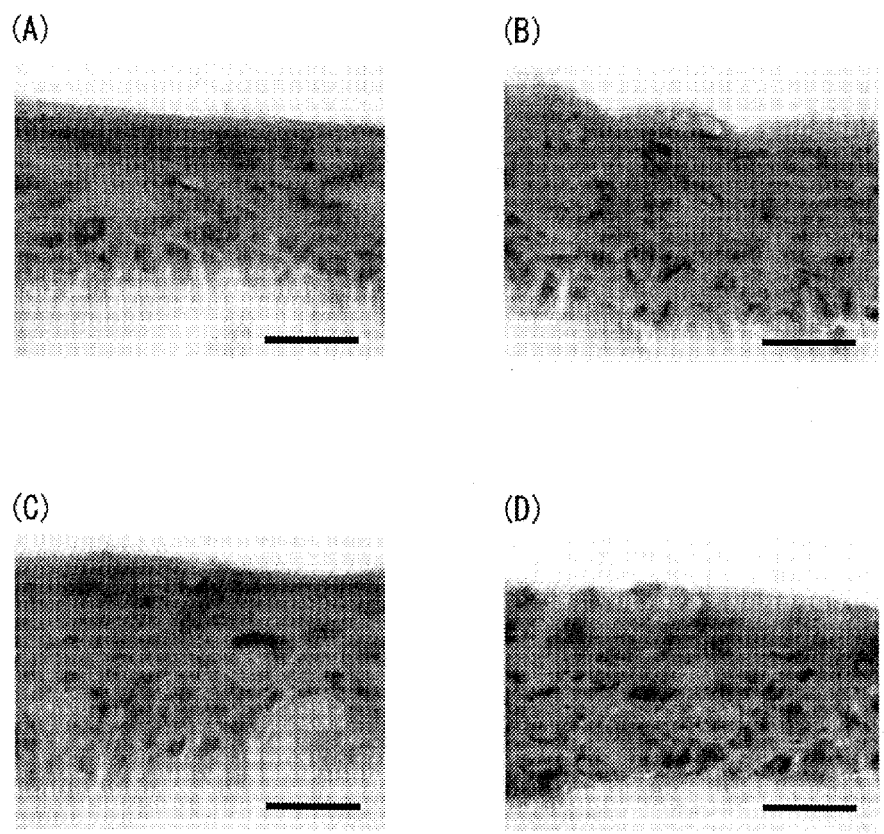
[FIG. 13] FIG. 13 (A) is a photograph serving as a drawing and showing the results obtained by observing the tissue morphology of the cell construct to which the sample of Experimental No. 36 is applied without applying a 0.5 volume % oleic acid-containing ethanol solution in Test Example 7.

FIG. 13 (A) shows the results obtained by observing the tissue morphology of the cell construct to which the sample of Experimental No. 36 was applied without applying a 0.5 volume % oleic acid-containing ethanol solution in Test Example 7. FIG. 13 (B) shows the results obtained by observing the tissue morphology of the cell construct to which a 0.5 volume % oleic acid-containing ethanol solution and the sample of Experimental No. 37 were applied in Test Example 7. FIG. 13 (C) shows the results obtained by observing the tissue morphology of the cell construct to which a 0.5 volume % oleic acid-containing ethanol solution and the sample of Experimental No. 38 were applied in Test Example 7. FIG. 13 (D) shows the results obtained by observing the tissue morphology of the cell construct to which a 0.5 volume % oleic acid-containing ethanol solution and the sample of Experimental No. 39 were applied in Test Example 7. In the figure, the scale bar has a length of 50 μm.

The results shown in FIGS. 13 (A) and (C) indicate that the cell construct to which a 0.5 volume % oleic acid-containing ethanol solution and the sample of Experimental No. 38 containing a cyclic peptide compound were applied had no nucleus as in the cell construct in which the sample of Experimental No. 36 was used. Accordingly, this indicates that the cyclic peptide compound can inhibit parakeratosis caused by oleic acid.

On the other hand, the results shown in FIG. 13 (D) indicate that in the cell construct to which a 0.5 volume % oleic acid-containing ethanol solution and the sample of Experimental No. 39 containing a linear peptide were applied, a nucleus could be observed. Therefore, this indicates that the linear peptide cannot inhibit parakeratosis caused by oleic acid.

Test Example 8

The same procedure as in Test Example 7 was performed, except that, of the cyclic peptide compounds represented by formula (I), a compound other than the cyclic peptide compound obtained in Example 1 was used in place of the cyclic peptide compound obtained in Example 1. The tissue morphology of the cell construct was observed by a phase-contrast microscope.

Consequently, results similar to those obtained when the cyclic peptide compound obtained in Example 1 was used could be obtained.

The results indicate that according to the cyclic peptide compound of the present invention or the pharmaceutically acceptable salt thereof, the generation of abnormalities in human skin conditions caused by epimorphin or oleic acid, particularly parakeratosis, can be inhibited. Accordingly, it is suggested that the cyclic peptide compound of the present invention or the pharmaceutically acceptable salt thereof can be used for ameliorating abnormalities in human skin conditions caused by parakeratosis.

Sequence Listing Free Text

SEQ ID NO: 1 is a sequence of a cyclic peptide compound. The sixth cysteinyl group and the seventh cysteinyl group are linked through a disulfide or peptide bond. The first Xaa is optionally substituted Ser, optionally substituted Thr, or optionally substituted Tyr. The second Xaa is optionally substituted Ile, optionally substituted Val, or optionally substituted Leu. The third Xaa is optionally substituted Asn, optionally substituted Gln, optionally substituted Asp, or optionally substituted Glu. The fourth Xaa is optionally substituted Asn, optionally substituted Gln, optionally substituted Asp, or optionally substituted Glu. The fifth Xaa is optionally substituted Ser, optionally substituted Thr, or optionally substituted Tyr. The first Xaa and the seventh Cys are not terminal residues but are linked to each other via $R^1$ ($R^1$ is represented by $-CO-(CH_2)_n-NH-$ or $-NH-(CH_2)_n-CO-$, wherein n is an integer of 1 to 10).

SEQ ID NO: 2 is a partial sequence of a straight-chain peptide or a cyclic peptide compound.

SEQ ID NO: 3 is a sequence of a straight-chain peptide.

SEQ ID NO: 4 is a sequence of amino acid chain before being subjected to cyclization for producing a cyclic peptide compound. The first Cys and the second Xaa are linked to each other via $R^1$ ($R^1$ is represented by $-CO-(CH_2)_n-NH-$ or $-NH-(CH_2)_n-CO-$, wherein n is an integer of 1 to 10). The second Xaa is optionally substituted Ser, optionally substituted Thr, or optionally substituted Tyr. The third Xaa is optionally substituted Ile, optionally substituted Val, or optionally substituted Leu. The fourth Xaa is optionally substituted Asn, optionally substituted Gln, optionally substituted Asp, or optionally substituted Glu. The fifth Xaa is optionally substituted Asn, optionally substituted Gln, optionally substituted Asp, or optionally substituted Glu. The sixth Xaa is optionally substituted Ser, optionally substituted Thr, or optionally substituted Tyr.

SEQ ID NO: 6 is a T7 tag sequence.

SEQ ID NO: 7 is a sequence of IL-2 signal peptide.

SEQ ID NO: 8 is a sequence of amino acid sequence before being subjected to cyclization for producing a cyclic peptide compound.

The invention claimed is:

1. A cyclic peptide compound represented by Formula (I):

$$\text{Xaa}^1\text{—Xaa}^2\text{—Xaa}^3\text{—Xaa}^4\text{—Xaa}^5\text{—Cys—Cys} \qquad (I)$$
$$\underbrace{\phantom{XXXXXXXXXXXXXXXXXXXXXXX}}_{R^1}$$

or a pharmacologically acceptable salt thereof, wherein
Xaa$^1$ and Xaa$^5$ are each independently optionally substituted seryl, optionally substituted threonyl, or optionally substituted tyrosinyl;
Xaa$^2$ is optionally substituted isoleucyl, optionally substituted valyl, or optionally substituted leucyl;
Xaa$^3$ and Xaa$^4$ are each independently optionally substituted asparaginyl, optionally substituted glutaminyl, optionally substituted aspartyl, or optionally substituted glutamyl;
Cys is cysteinyl; and
R$^1$ is a group represented by either Formula (II):

$$\text{—CO—(CH}_2)_n\text{—NH—} \qquad (II),$$

wherein n is an integer of 1 to 10, or Formula (III):

$$\text{—NH—(CH}_2)_n\text{—CO—} \qquad (III)$$

wherein n is an integer of 1 to 10; and in Formula (I), the linkage between Cys and Cys is a peptide bond or a disulfide bond, and the other linkages are peptide bonds.

2. The cyclic peptide compound or a pharmacologically acceptable salt thereof according to claim 1, wherein in Formula (I), Xaa$^1$ is seryl, Xaa$^2$ is isoleucyl, Xaa$^3$ is glutamyl, Xaa$^4$ is glutaminyl, Xaa$^5$ is seryl, and R$^1$ is a group represented by Formula (III) wherein n is 1.

3. The cyclic peptide compound or a pharmacologically acceptable salt thereof according to claim 1 or 2, wherein in Formula (I), Cys and Cys are linked through a disulfide bond.

4. A method for producing a cyclic peptide compound represented by Formula (I):

$$\text{Xaa}^1\text{—Xaa}^2\text{—Xaa}^3\text{—Xaa}^4\text{—Xaa}^5\text{—Cys—Cys} \qquad (I)$$
$$\underbrace{\phantom{XXXXXXXXXXXXXXXXXXXXXXX}}_{R^1}$$

or a pharmacologically acceptable salt thereof, wherein
Xaa$^1$ and Xaa$^5$ are each independently optionally substituted seryl, optionally substituted threonyl, or optionally substituted tyrosinyl;
Xaa$^2$ is optionally substituted isoleucyl, optionally substituted valyl, or optionally substituted leucyl;

Xaa$^3$ and Xaa$^4$ are each independently optionally substituted asparaginyl, optionally substituted glutaminyl, optionally substituted aspartyl, or optionally substituted glutamyl;
Cys is cysteinyl; and
R$^1$ is a group represented by either Formula (II):

$$\text{—CO—(CH}_2)_{n\text{—NH—}} \qquad (II),$$

wherein n is an integer of 1 to 10, or Formula (III):

$$\text{—NH—(CH}_2)_n\text{—CO—} \qquad (III)$$

wherein n is an integer of 1 to 10; and in Formula (I), the linkage between Cys and Cys is a peptide bond or a disulfide bond, and the other linkages are peptide bonds,
the method comprising cyclizing a compound represented by Formula (IV):

$$\text{Cys-R}^1\text{-Xaa}^1\text{-Xaa}^2\text{-Xaa}^3\text{-Xaa}^4\text{-Xaa}^5\text{-Cys} \qquad (IV),$$

wherein Xaa$^1$, Xaa$^2$, Xaa$^3$, Xaa$^4$, Xaa$^5$, Cys, and R$^1$ are the same as Xaa$^1$, Xaa$^2$, Xaa$^3$, Xaa$^4$, Xaa$^5$, Cys, and R$^1$ of Formula (I).

5. The production method according to claim 4, wherein the cyclic peptide compound is a compound represented by Formula (I) wherein Xaa$^1$ is seryl, Xaa$^2$ is isoleucyl, Xaa$^3$ is glutamyl, Xaa$^4$ is glutaminyl, Xaa$^5$ is seryl, and R1 is a group represented by Formula (III) wherein n is 1, and
wherein a compound used as a starting material is a compound represented by Formula (IV) wherein Xaa$^1$ is seryl, Xaa$^2$ is isoleucyl, Xaa$^3$ is glutamyl, Xaa$^4$ is glutaminyl, Xaa$^5$ is seryl, and R$^1$ is a group represented by Formula (III).

6. The production method according to claim 4 or 5, wherein the cyclic peptide compound is a compound in which Cys and Cys of Formula (I) are linked through a disulfide bond, and wherein the cyclization is performed by oxidative crosslinking of the thiol groups of the cysteines at both ends of the compound represented by Formula (IV).

7. The cyclic peptide compound or a pharmacologically acceptable salt thereof according to claim 1, wherein in Formula (I), Xaa$^1$ is seryl, Xaa$^2$ is isoleucyl, Xaa$^3$ is glutamyl, Xaa$^4$ is glutaminyl, Xaa$^5$ is seryl, and R$^1$ is a group represented by Formula (III) wherein n is 5 or 8.

8. A pharmaceutical composition comprising the cyclic peptide compound or a pharmacologically acceptable salt thereof of claim 1 as an active ingredient, the pharmaceutical composition being in an oral dosage form.

9. A method for treating diseases or disorders induced by epimorphin or resulting from overexpression of epimorphin, comprising a step of administering orally the cyclic peptide compound or a pharmacologically acceptable salt thereof of claim 1 to a patient with disease or disorders induced by epimorphin or resulting from overexpression of epimorphin, wherein the disease or disorders induced by epimorphin or resulting from overexpression of epimorphin are chronic arteriosclerosis obliterans, Buerger's disease, or damaged organs.

10. The production method according to claim 4, wherein the cyclic peptide compound is a compound represented by Formula (I) wherein $Xaa^1$ is seryl, $Xaa^2$ is isoleucyl, $Xaa^3$ is glutamyl, $Xaa^4$ is glutaminyl, $Xaa^5$ is seryl, and $R^1$ is a group represented by Formula (III) wherein n is 5 or 8, and wherein a compound used as a starting material is a compound represented by Formula (IV) wherein $Xaa^1$ is seryl, $Xaa^2$ is isoleucyl, $Xaa^3$ is glutamyl, $Xaa^4$ is glutaminyl, $Xaa^5$ is seryl, and $R^1$ is a group represented by Formula (III).

* * * * *